(12) United States Patent
D'Cruz et al.

(10) Patent No.: US 6,407,078 B1
(45) Date of Patent: *Jun. 18, 2002

(54) AZT DERIVATIVES EXHIBITING SPERMICIDAL AND ANTI-VIRAL ACTIVITY

(75) Inventors: Osmond D'Cruz, Maplewood; Faith M. Uckun, White Bear Lake; Taracad Venkatachalam, St. Anthony, all of MN (US)

(73) Assignee: Parker Hughes Institute, Roseville, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/497,297

(22) Filed: Feb. 3, 2000

Related U.S. Application Data

(63) Continuation of application No. 09/047,609, filed on Mar. 25, 1998, now Pat. No. 6,191,120.

(51) Int. Cl.$^7$ .............................................. A61K 31/70
(52) U.S. Cl. ......................... 514/50; 514/51; 536/26.8; 536/28.54; 536/28.55
(58) Field of Search .................. 514/50, 51; 536/26.8, 536/28.2, 28.54, 28.55

(56) References Cited

U.S. PATENT DOCUMENTS

| | | | | |
|---|---|---|---|---|
| 4,707,362 A | * | 11/1987 | Nuwayer | 424/433 |
| 4,841,039 A | | 6/1989 | Chu et al. | 536/28.2 |
| 5,069,906 A | * | 12/1991 | Cohen et al. | 424/430 |
| 5,595,980 A | * | 1/1997 | Brode et al. | 514/57 |
| 5,659,023 A | | 8/1997 | Alexander et al. | 536/22.1 |
| 5,672,698 A | | 9/1997 | Chen et al. | 536/55.3 |
| 5,750,729 A | | 5/1998 | Alexander et al. | 549/216 |

FOREIGN PATENT DOCUMENTS

| | | | |
|---|---|---|---|
| JP | 6189998 | * | 7/1994 |
| WO | 9414831 | * | 7/1994 |
| WO | WO 96/29336 | | 9/1996 |
| WO | 9742962 | * | 11/1997 |

OTHER PUBLICATIONS

McGuigan et al.(I), "Phosphoramidates as Potent Prodrugs of Anti–HIV Nucleotide Studies in the Amino Region," *Antiviral Chemistry & Chemotherapy*, 7(1), 31–36 (1996).*

McGuigan et al.(II), "Phosphoramidate Derivatives of AZT as Inhibitors of HIV: Studies on the Carboxyl Terminus," *Antiviral Chemistry & Chemotherapy*, 4(2), 97–101 (1993).*

McGuigan et al.(III), "Aryl Phosphate Derivates of AZT Inhibit HIV Replication in Cells Where the Nucleoside Is Poorly Active," *Bioorganic & Medicinal Chemistry Letters*, 2(7), 701–704 (1992).*

Wang et al., "In Vivo Biodistribution, Pharmacokinetic Parameters, and Brain Uptake of 5–Halo–6–methoxy (or ethoxy)–5,6–dihydro–3'–azido–3'–deoxythymidine Diastereoisomers as Potenial Prodrugs of 3'–Azido–3'deoxythymidine," *J. Medicinal Chemistry*, 39(4), 826–833 (Feb. 16, 1996).*

Bourinbaiar et al.(I), "Anti–HIV Effect of Gramicidin In Vitro: Potenial for Spermicide Use," *Life Sciences*, 54(1), PL5–9 (1994).*

Bourinbaiar et al.(II), "Comparative In Vitro Study of Contraceptive Agents with Anti–HIV Activity: Gramicidin, Nonoxyl–9, and Gossypol," *Contraception*, 49(2), 131–137 (Feb., 1994).*

Burkman, "Discrimination Between Nonhyperactivated and Classical Hyperactivated Motility Patterns in Human Spermatozoa Using Computerized Analysis," *Fertility and Sterility*, 55(2), 363–371 (Feb., 1991).*

D'Cruz et al. (I), "$\beta_2$–Integrin (CD11b/CD18) Is the Primary Adhesive Glycoprotein Complex Involved in Neutrophil–Mediated Immune Injury to Human Sperm," *Biology of Reproduction*, 53(5), 1118–1130 (Nov., 1995).*

D'Cruz et al. (II), "Spermicidal Activity of Metallocene Complexes Containing Vanadium (IV) in Humans," *Biology of Reproduction*, 58(6), 1515–1526 (Jun., 1998).*

D'Cruz et al. (III), "Acyl Phosphate Derivatives of Bromo–Methoxy–Azidothymidine Are Dual Function Spermicides with Potent Anti–Human Immunodeficiency Virus [Activity]," *Biology of Reproduction*, 59, 503–515 (1998).*

Dicker et al., "The Value of Repeat Hysteroscopic Evaluation in Patients with Failed In Vitro Fertilization Transfer Cycles," *Fertilizaty and Sterility*, 58(4), 833–835 (Oct., 1992).*

Erice et al., "Human Immunodeficiency Virus Type 1 Activity of an Anti–CD4 Immunoconjugate Containing Pokeweed Antiviral Protein," *Antimicrobial Agents & Chemotherapy*, 37(4), 835–838 (Apr., 1983).*

(List continued on next page.)

*Primary Examiner*—Gary Geist
*Assistant Examiner*—L. E. Crane
(74) *Attorney, Agent, or Firm*—Merchant & Gould P.C.

(57) ABSTRACT

Contraceptive activity as well as anti-viral protection can be provided by contraceptive compositions containing a pyrimidine-based nucleoside or nucleotide exhibiting spermicidal or sperm-immobilizing activity. In one example, the active ingredient contains a thymine ring (e.g. AZT) that has 5-halo, 6-alkoxy substitution. Additional improvements in anti-HIV activity for certain AZT derivatives are seen by providing the pentose ring of AZT with aryl phosphate substitution.

25 Claims, 8 Drawing Sheets

OTHER PUBLICATIONS

Erlandsen et al., "Membrane Fixation for High–Resolution Low–Voltage SEM: Studies on Giardia, Rat Spermatozoa, and Mouse Microphages," *Scanning*, 11(4), 169–175 (Jul./Aug., 1989).*

Kumar et al., "Synthesis, In Vitro Biology Stability, and Anti–HIV Activity of 5–Halo–6–alkoxy (or azido)–5, 6–dihydro–3'–azido–3'–deoxythymidine," *J. Medicinal Chemistry*, 37(25), 4297–4305 (Dec. 9, 1994).*

Wiebe et al., "5–Halo–6–alkoxy–5,6–dihydro–pyrimidine Nucleosides: Antiviral Nucleosides or Nucleoside Prodrugs," *Nucleosides & Nucleotides*, 14(3–5), 501–505 (May–Jun.–Jul., 1995).*

McGuigan et al. (IV), "Intracellular Delivery of Bioactive AZT Nucleotides by Aryl Phosphate Derivatives of AZT," *Journal of Medicinal Chemistry*, 36(8), 1048–1052 (Apr. 16, 1993).*

McGuigan et al. (V), "Aryl Phosphoramidate Derivatives of d4T Have Improved Anti–HIV Efficacy in Tissue Culture and May Act by the Generation of a Novel Intracellular Metabolite," *Journal of Medicinal Chemistry*, 39(8), 1748–1753 (Apr. 12, 1996).*

McGuigan et al. (VI), "Phosphoramidate Derivatives of d4T with Improved Anti–HIV Efficacy Retain Full Activity in Thymidine Kinase–Deficient Cells," *Bioorganic & Medicinal Chemistry Letters*, 6(10), 1183–1186 (May 21, 1996).*

Jan et al., "Synthesis and Dual Function (5R,6R)– and (5S,6S)–5–Bromo–6–methoxy–5, 6–dihydro–AZT–5'–(para–bromophenyl methoxyalaninyl Phosphate) as Novel Spermcidal and Anti–HIV Agent," *Antiviral Chemistry & Chemotherapy*, 10, 39–46 (Jul. 9, 1999).*

Niruthisard et al., "The Effects of Frequent Nonoxyl–9 Use on the Vaginal and Cervical Mucosa," *Secually Transmitted Diseases*, 18(3), 176–179 (Jul.–Sep., 1991).*

Stoffel et al., "Improved Preservation of Rat Epidermal Sperm for High–Resolution Low–Voltage Scanning Electron Microscopy (HR–LVSEM)," *Molecular Reproduction and Development*, 34(2), 172–182 (Feb., 1993).*

Typhonas et al., "Morphologic Evidence for Vaginal Toxicity of Delfen Contraceptive Cream in the Rat," *Toxicology Letters*, 20(3), 289–295 (Mar., 1984).*

Uckum et al., "TXU (Anti–CD7)–Pokeweed Antiviral Protein as a Potent Inhibitor of Human Immunodeficiency Virus," *Antimicrobial Agents & Chemotherapy*, 42(2), 383–388 (Feb. 1998).*

Wilborn et al., "Scanning Electron Microscopy of Human Spermatozoa After Incubation with the Spermicide Nonoxyl–9," *Fertility and Sterility*, 39(5), 717–719 (May, 1983).*

Zarling et al., "Inhibition of HIV Replication by Pokeweed Antiviral Protein Targeted to CD4+ Cells by Monoclonal Antibodies," *Nature*, 347(6288), 92–95 (Sep. 6, 1990).*

Siddiqui et al., "Design and Synthesis of Lipophilic Phosphoramidite d4T–MP Prodrugs Expressing High Potency Against HIV in Cell Culture: Structural Determinants for In Vitro Activity and QSAR," *Journal of Medicinal Chemistry*, 42(20), 4122–4128 (Oct. 7, 1999); WEB published on Sep. 21, 1999.*

Alexander, P. et al., "Synthesis and Antiviral Activity of Pyranosylphosphonic Acid Nucleotide Analogues", *J. Med. Chem.*, 39: 1321–1330 (Mar. 15, 1996).

Balzarini, J. et al, "Differential Patterns of Intracellular Metabolism of 2', 3'–dideoxythymidine and 3'–Dideoxythymidine, Two Potent Anti–human Immunodeficiency Virus Compounds", *J. Biol.Chem.*, 264(11):6127–6133 (Apr. 15, 1989).

Furman, P. et al, "Phosphorylation of 3'–azido–3'–deoxythymidine and selective interaction of the 5'–triphosphate with Human Immunodeficiency Virus Reverse Transciptase", *Proc. Natl. Acad. Sci. USA*, vol. 83, pp. 8333–8337 (Nov. 1986).

Mansuri, M. et al., "1–(2, 3–Dideoxy–β–D–glycero–pent–2–enofuranosyl) Thymine. A higly Potent and Selective Anti–HIV Agents", *J. Med. Chem.*, 32(2):461–466 (Feb. 1989).

McGuigan, C. et al., "Aryl Phosphate Derivatives of AZT Retain Activity HIV1 in Cell Lines Which are Resistant to the Action of AZT", *Antiviral Research*, 17(4):311–321 (Apr. 1, 1992).

McIntee, E. et al.; "Probing the Mechanism of Action and Decomposition of Amino Acid Phosphomonoester Amidates of Antiviral Nucleoside Prodrugs", *J. Med. Chem.*, 40(21):3323–3331 (Oct. 10, 1997.

Siddiqui, A. et al., "The Presence of Substituents on the Aryl Moiety of the Aryl Phosphoramidate Derivative of d4T Enhances Anti–HIV Efficacy in Cell Culture: A Structure—Activity Relationship", *J. Med. Chem.*, 42:393–399 (1999).

Vig, R. et al., "D4T–5'[p–Bromophenyl Methoxyalaninyl Phosphate] as a Potent and Non–Toxic Anti–Human Immunodeficiency Virus Agent", *Antiviral Chem. Chemother.*, vol. 9(5), pp. 445–448 (1998).

Jan, S. et al., "AZT–5'–(p–bromophenyl methoxyalaninyl phosphate) as a potent and non–toxic anti–human immunodeficiency virus agent," *Antiviral Chemistry & Chemotherapy*, vol. 10, pp. 47–52 (©1999 International Medical Press).

Venkatachalam, T. K. et al., "Enhancing Effects of a Mono–Bromo Substitution at the Para Position of the Phenyl Moiety on the Metabolism and Anti–HIV Activity of D4T–Phenyl Methoxyalaninyl Phosphate Derivatives," *Bioorganic & Medicinal Chemistry Letters*, vol. 8, pp. 3121–3126 (1998).

Vig. R. et al., "Aryl phosphate derivatives of 3'–deoxythymidine are not potent anti–human imunodeficiency virus agents," *Antiviral Chemistry & Chemotherapy*, vol. 9, pp. 439–443 (©1998 International Medical Press).

* cited by examiner

A.

| Group A Compound | $R_1$ | $R_2$ | $R_3$ | $IC_{50}$ (μM) | $EC_{50}$ (μM) |
|---|---|---|---|---|---|
| AZT | $N_3$ | - | - | 0.006 | >300 |
| WHI-01 | $N_3$ | Br | OMe | 0.006 | 104 |
| WHI-02 | $NH_2$ | - | - | 0.350 | >300 |
| WHI-03 | $NH_2$ | Br | OMe | 0.250 | 12 |

B.

| Group B Compound | $R_1$ | $R_2$ | $R_3$ | $R_4$ | $R_5$ | $IC_{50}$ (μM) | $EC_{50}$ (μM) |
|---|---|---|---|---|---|---|---|
| WHI-04 | $N_3$ | Br | OMe | H | H | 0.035 | 35 |
| WHI-05 | $N_3$ | Br | OMe | OMe | H | 0.050 | 29 |
| WHI-06 | $N_3$ | Br | OMe | F | H | 0.070 | 15 |
| WHI-07 | $N_3$ | Br | OMe | Br | H | 0.005 | 6 |
| WHI-08 | $N_3$ | - | - | Br | H | 0.006 | >300 |
| WHI-09 | $N_3$ | - | - | OMe | H | 0.057 | >300 |
| WHI-10 | $N_3$ | - | - | F | H | 0.029 | >300 |
| WHI-11 | H | Br | OMe | Br | H | 1.924 | 58 |
| WHI-12 | H | Br | OMe | H | H | 3.322 | 42 |
| N-9 | NA | NA | NA | NA | NA | 2.195 | 81 |

| Treatment | Zona-free Hamster Eggs | |
|---|---|---|
| | Binding* | Penetration†‡ |
| None | 15.0 ± 14.8 | 68/121 (56.2%) |
| WHI-05 | | |
| 25 µM | 5.6 ± 7.0 | 7/28 (25.0%) |
| 100 µM | 0.1 ± 0.4 | 0/15 (0%) |
| WHI-07 | | |
| 25 µM | 4.1 ± 7.3 | 11/88 (12.5%) |
| 100 µM | 5.8 ± 7.0 | 10/59 (16.9%) |

| Treatment | PMN† influx | Disruption of epithelia |
|---|---|---|
| Control | | |
| 5 days | 0/5 | 0/5 |
| 20 days | 0/5 | 0/5 |
| WHI-07 | | |
| 5 days | 0/5 | 0/5 |
| 20 days | 0/5 | 0/5 |
| N-9 | | |
| 5 days | 5/5 | 5/5 |
| 20 days | 4/5 | 4/5 |

AZT DERIVATIVES EXHIBITING SPERMICIDAL AND ANTI-VIRAL ACTIVITY

This application is a Continuation of application Ser. No. 09/047,609, filed Mar. 25, 1998, now U.S. Pat. No. 6,191,125 which application(s) are incorporated herein by reference.

FIELD OF THE INVENTION

The present invention is directed to the use of AZT derivatives and its analogs in providing contraceptive, e.g. spermicidal, effects. In one particular embodiment, the present invention is directed to novel dual-function derivatives of AZT that exhibit spermicidal activity and maintain potent anti-HIV activity.

BACKGROUND OF THE INVENTION

The known spermicidal agents, nonoxynol-9 (N9) and gramicidin, exert their effects via a detergent-like ability to damage the sperm plasma membrane, perturb its conformation and destroy its semi-permeable nature thereby impairing the sperm motility and egg fertilizing functions (Wilborn, et al., *Fertil Steril* 1983; 39:717–719; Bourinbaiar, et al., *Life Sci* 1994; 54:PL 5–9). Because of their non-specific membrane disruptive properties, such vaginal spermicides have been shown to damage the cervicovaginal epithelium, as well, which may lead to a lower degree of protection from sexually transmitted diseases (Niruthisard, et al., *Sex Transm Dis* 1991; 18:176–179). A vaginal contraceptive that does not function with the non-specific membrane toxicity mediated by detergent-type action of the currently available vaginal contraceptives would be desirable.

In addition, the dangers of sexually-transmitted diseases have been widely recognized. However, despite the educational and preventive measures taken to date, the spread of diseases such as HIV remains a serious health problem. It would be desirable to provide a contraceptive that also provides some protection against sexually-transmitted diseases such as HIV, especially to reduce the risks for women who otherwise would be at high risk of acquiring such diseases by heterosexual transmission.

SUMMARY OF THE INVENTION

While AZT has been widely studied for its activity against HIV infection, AZT itself has not been recognized as having any contraceptive, for example spermicidal and/or sperm-immobilizing, activity. The present invention provides AZT derivatives that are useful as contraceptive agents and products and methods using them. Examples of such products include vaginal foams, creams, lotions or gels, sponges or other vaginal inserts, and condom lubricating compositions. The present invention also is directed to certain AZT derivatives that exhibit the contraceptive properties while maintaining activity against HIV.

One aspect of the present invention is directed to AZT derivatives that include 5-halo and 6-alkoxy substitution on the thymine ring of AZT and exhibit contraceptive properties.

A very important aspect of the present invention is directed to providing a contraceptive effect using novel dual-function AZT derivatives with both anti-HIV and spermicidal activity that include 5-halo and 6-alkoxy substitution on the thymine ring of AZT and substitution on the pentose ring of AZT that facilitates entry of the compound into a cell. For example, among others, the substitution on the pentose ring can be with a phosphate group, which may be further substituted with an aryl-containing group, and the aryl group itself can be further substituted. In the above aspects of the invention, the azide group on the pentose ring of AZT can be replaced with $NH_2$, which optionally can be substituted, or the azide group could be replaced with halo, CN, or COOH.

A further aspect of the present invention is directed to contraceptive products that use a spermicidal AZT derivative as an active agent, and to the production of such contraceptive products.

A still further aspect of the present invention is directed to a method of contraception that includes a step of contacting sperm with a spermicidal AZT derivative, for example by means of a contraceptive product of this invention as discussed above.

BRIEF DESCRIPTION OF THE DRAWINGS

FIGS. 3A to 3D are confocal microscopic images of drug treated sperm. FIGS. 3A' to 3D' are high-resolution low-voltage scanning electron microscopic images and FIGS. 3A" to 3D" are transmission electron microscopic images of drug treated sperm. FIGS. 3A, 3A', and 3A" are images of sperm treated with 1% DMSO for three hours. FIGS. 3B, 3B', and 3B" are images of sperm treated with 100 $\mu$M WHI-05 for three hours. FIGS. 3C, 3C',3C" are images of sperm treated with 100 $\mu$M WHI-07 for three hours. FIGS. 3D, 3D', 3D" are images of sperm treated with 100 $\mu$M N-9 for three hours.

FIG. 4B is a table showing the dose dependent effect of some AZT derivatives of the present invention on the binding and penetration ability of sperm.

FIG. 5A shows that there was no significant inflammatory response or membrane disruption of squamous epithelia in mice treated with WHI-07. FIG. 5B shows that there was significant inflammatory response and membrane disruption of squamous epithelia in mice treated with N-9. FIG. 5C is a laser scanning confocal image of cervicovaginal epithelia in mice treated with WHI-07. FIG. 5D is the laser scanning confocal image of cervicovaginal epithelia in mice treated with N-9.

FIG. 5E is a table showing the reduction in inflammation of cervicovaginal tissue and disruption of the epithelial lining from an AZT derivative of the present invention versus N-9.

DETAILED DESCRIPTION

Figure 1A:
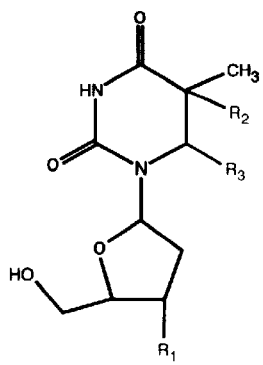
FIG. 1A compares the anti-HIV and spermicidal activity of AZT and various AZT derivatives of the present invention.

In the course of pursuing active agents having improved activity against HIV, it was unexpectedly discovered that derivatives of AZT possess spermicidal and/or sperm-immobilizing activity and thus are useful as active agents for contraceptive products and methods. These derivatives are particularly useful in forming contraceptive products that can reduce the spread of sexually-transmitted diseases as well as inhibit conception.

In particular, AZT derivatives having contraceptive activity are provided by substituting the thymine ring of AZT with halo at the 5-position and alkoxy at the 6-position, particularly C1-3 alkoxy. The derivatives of this aspect of the present invention have the chemical structure illustrated below:

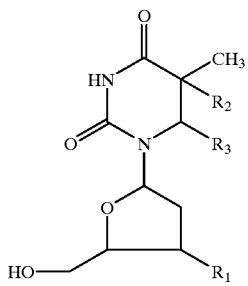

(I)

where $R_1$ is H, $N_3$, halo, CN, COOH or $NH_2$, $R_2$ is halo (particularly Cl, Br or I, and more particularly Br) and $R_3$ is alkoxy (particularly C1-3 alkoxy, and more particularly methoxy (—$OCH_3$)). The $NH_2$ group can be functionalized, for example with —$CH_3$, —$COCH_3$, —Ph, —COPh, and —$CH_2$Ph. Pharmaceutically acceptable salt or ester forms also can be used, such as sodium, potassium or ammonium salts.

In a further aspect of the present invention, the derivatives of formula (I) above include substitution on the AZT pentose ring member. The derivatives of this aspect of the present invention have the chemical structure illustrated below:

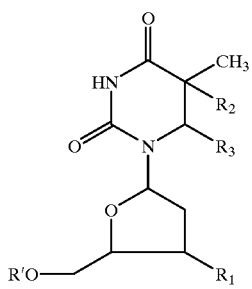

(II)

where $R_1$ is H, $N_3$, halo, CN, COOH or $NH_2$, $R_2$ is halo (particularly Cl, Br or I, and more particularly Br), $R_3$ is alkoxy (particularly C1-3 alkoxy, and more particularly methoxy (—$OCH_3$)) and R' is a group that facilitates the passage of the compound into a cell. As in Formula (I), the $NH_2$ group can be converted, for example to $NHCH_3$, $NHCOCH_3$, NHPh, NHCOPh, and $NHCH_2$Ph. The R' group can be, for example, a phosphate, lipid or fatty acid group. Alternatively, sperm-reactive antibodies or cytokines could be used to derivatize these compounds (as well as those of Formula (I)) at the R' or $R_1$ positions for targeted delivery. Pharmaceutically acceptable salt or ester forms, such as the sodium, potassium or ammonium salts, can be used as well.

In a further aspect of the invention, the R' group forms a phosphate group. The H of an —OH member of the phosphate can be replaced with C1-4 alkyl or aryl substituents (e.g. phenyl-, naphthyl- or anthracinyl-substitution), which optionally may be substituted, and SH or $NH_2$ groups can replace the OH of the phosphate, and in each of these cases a H of the $NH_2$ or SH can be replaced in the same manner as the H of the OH group discussed previously. The aryl phosphate group is surprisingly effective in maintaining excellent anti-HIV activity. A general structure of an exemplary aryl phosphate OR' group is illustrated below:

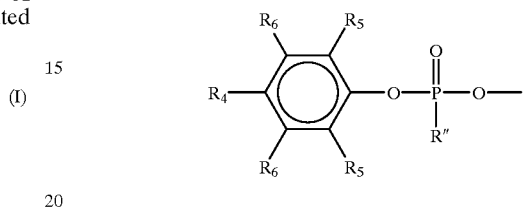

where $R_4$, $R_5$, and $R_6$ are the same or different and are selected from hydrogen, methyl, ethyl, fluoro, chloro, bromo, iodo, dichloro, dibromo, difluoro, trifluoromethyl, nitro, cyano, methoxy, trifluromethoxy and ethoxy, particularly hydrogen, fluoro, bromo and methoxy and R" is an amino acid residue that may optionally be substituted and/or esterified, for example an alaninyl group (—NHCH(Me)COOMe). In the case of the alaninyl group, the methyl group attached to the CH group can be substituted, for example with a phenyl group, and the methyl esterification can be replaced with other C2 or C3 esterification.

In the derivatives of the above formulae (I) and (II), when $R_1$ is $NH_2$, improved spermicidal (i.e. contraceptive) activity is seen versus the cases where $R_1$ is $N_3$. However, anti-HIV activity is decreased, although still remaining at a useful level. Of the $R_4$ substituents, bromo substitution provided the best spermicidal activity, followed by fluoro, methoxy and hydrogen in that order. The bromo $R_4$ substitution also showed the best anti-HIV activity, followed by hydrogen, methoxy and fluoro in that order.

All of the derivatives discussed herein are believed to yield useful metabolites in sperm cells. It will be readily apparent to those skilled in the art that other structures yielding the same metabolites as the AZT derivatives mentioned above, and structures functioning as precursors to the present structures, can be developed. The present invention should be considered to encompass these other structures. Examples of other structures that will yield the same metabolites are illustrated below:

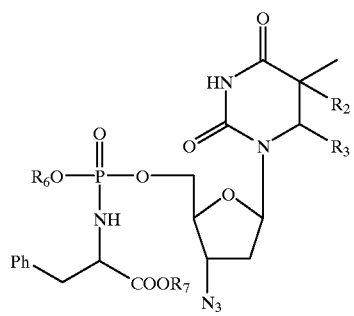

(a)

where R₂ is Cl, Br or I, R₃ is methoxy, ethoxy, or isopropoxy, R₆ is H, methyl, ethyl, propyl, butyl or CH₂Ph and R₇ is methyl, ethyl or propyl (b)

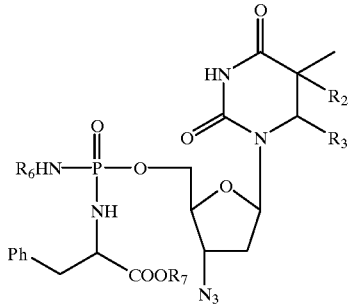

where R₂ is Cl, Br or I, R₃ is methoxy, ethoxy, or isopropoxy, R₆ is H, methyl, ethyl, propyl, butyl or CH₂Ph and R₇ is methyl, ethyl or propyl (c)

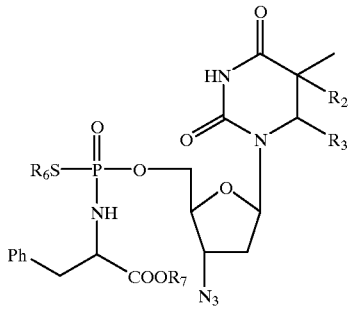

where R₂ is Cl, Br or I, R₃ is methoxy, ethoxy, or isopropoxy, R₆ is H, methyl, ethyl, propyl, butyl or CH₂Ph and R₇ is methyl, ethyl or propyl (d)

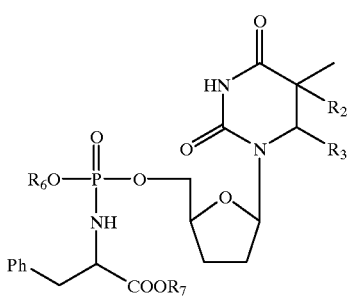

where R₂ is Cl, Br or I, R₃ is methoxy, ethoxy, or isopropoxy, R₆ is H, methyl, ethyl, propyl, butyl or CH₂Ph and R₇ is methyl, ethyl or propyl (e)

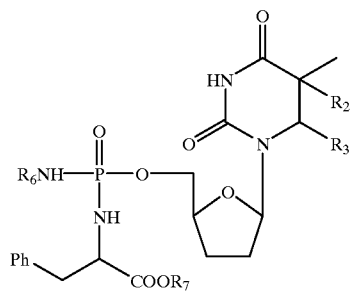

where R₂ is Cl, Br or I, R₃ is methoxy, ethoxy, or isopropoxy, R₆ is H, methyl, ethyl, propyl, butyl or CH₂Ph and R₇ is methyl, ethyl or propyl (f)

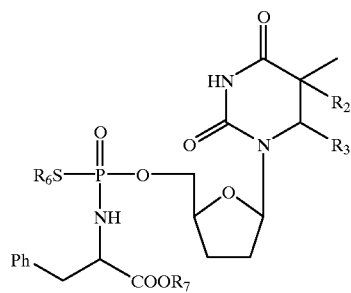

where R₂ is Cl, Br or I, R₃ is methoxy, ethoxy, or isopropoxy, R₆ is H, methyl, ethyl, propyl, butyl or CH₂Ph and R₇ is methyl, ethyl or propyl (g)

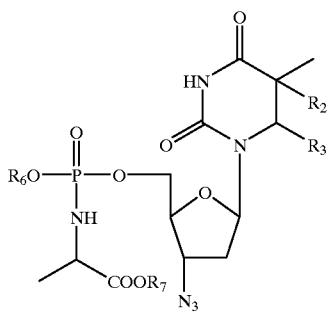

where R₂ is Cl, Br or I, R₃ is methoxy, ethoxy, or isopropoxy, R₆ is H, methyl, ethyl, propyl, butyl or CH₂Ph and R₇ is methyl, ethlyl or propyl (h)

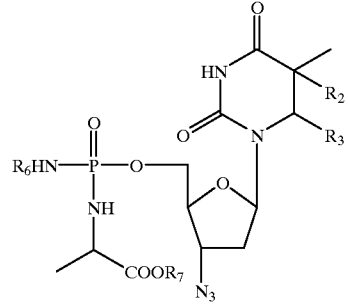

where $R_2$ is Cl, Br or I, $R_3$ is methoxy, ethoxy, or isopropoxy, $R_6$ is H, methyl, ethyl, propyl, butyl or $CH_2Ph$ and $R_7$ is methyl, ethyl or propyl

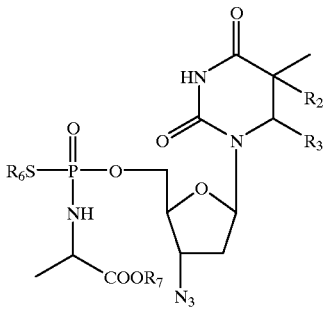
(i)

where $R_2$ is Cl, Br or I, $R_3$ is methoxy, ethoxy, or isopropoxy, $R_6$ is H, methyl, ethyl, propyl, butyl or $CH_2Ph$ and $R_7$ is methyl, ethyl or propyl

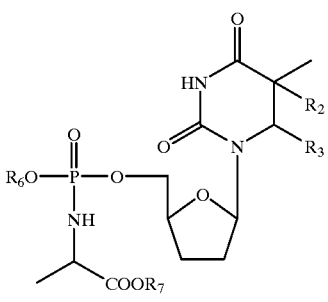
(j)

where $R_2$ is Cl, Br or I, $R_3$ is methoxy, ethoxy, or isopropoxy, $R_6$ is H, methyl, ethyl, propyl, butyl or $CH_2Ph$ and $R_7$ is methyl, ethyl or propyl

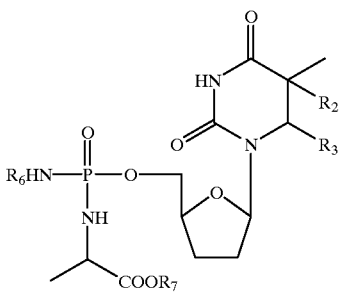
(k)

where $R_2$ is Cl, Br or I, $R_3$ is methoxy, ethoxy, or isopropoxy, $R_6$ is H, methyl, ethyl, propyl, butyl or $CH_2Ph$ and $R_7$ is methyl, ethyl or propyl

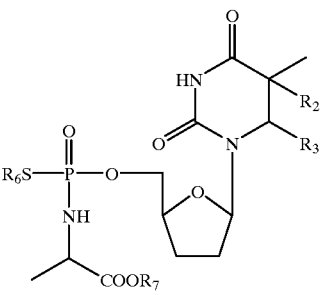
(l)

where $R_2$ is Cl, Br or I, $R_3$ is methoxy, ethoxy, or isopropoxy, $R_6$ is H, methyl, ethyl, propyl, butyl or $CH_2Ph$ and $R_7$ is methyl, ethyl or propyl.

While the present invention has been illustrated with respect to the thymine-containing nucleoside AZT and its derivatives, the 5-halogen and 6-alkoxy substitution providing contraceptive effects also will be effective for other nucleosides and nucleotides based on the pyrimidine ring system, of which thymine is one example. These other nucleosides can include ring members such as uracil or cytosine rings, for example, which are suitable for substitution in the same manner as thymine.

The AZT derivatives with 5-bromo and 6-methoxy substitution on the thymine ring can be prepared using known techniques. See R. Kumar et al. *J. Med. Chem.* 37, 4297 (1994); L. Wang et al. *J. Med. Chem.* 39, 826 (1996). Similarly, the aryl phosphate derivatives can be prepared using known phosphorochloridate chemistry techniques. See C. McGuigan et al. *J. Med. Chem.* 36, 1048 (1993); *J. Med. Chem.* 39, 1748 (1996); *Biorg. Med. Chem. Lett.* 6, 1183 (1996). The conversion of the azide group, for example to the $NH_2$ group, can be accomplished by known techniques. See *J. Med. Chem.*, 21, 109 (1978).

An exemplary synthetic scheme is illustrated below.

Synthetic Scheme I

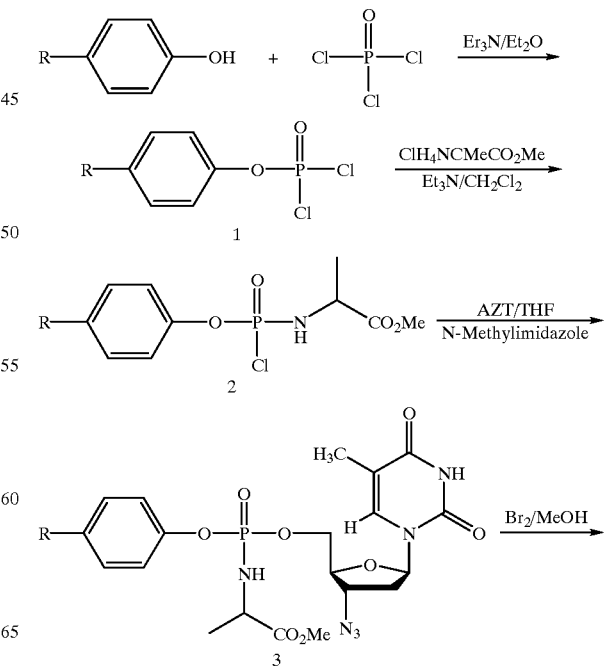

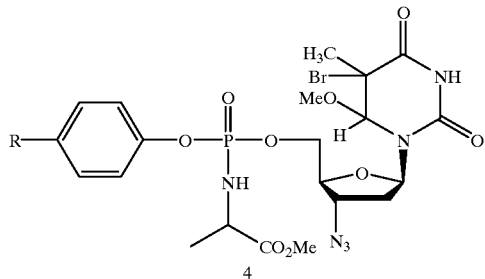

a) R = MeO, b) R = Br

Compound 3a was prepared according to known literature procedures. Compound 3a was treated with BrOMe to afford a diastereomeric mixture (approximately 2:1) of (5R,6R)-5-bromo-6-methoxy-5,6-dihydro-3'-azidothymidine 5'-(p-methoxyphenyl methoxyalaninyl phosphate) and (5S,6S)-5-bromo-6-methoxy-5,6-dihydro-3'-azidothymidine 5'-(p-methoxyphenyl methoxyalaninyl phosphate) (4a). The preparation of 3b was started with commercially available p-bromophenol and phosphorus oxychloride in ethyl ether, to obtain intermediate 1b. Intermediate 1b is coupled with alanine, to afford intermediate 2b. Intermediate 2b is further coupled with AZT under catalysis of N-methylimidazole, to obtain compound 3b. Compound 3b was treated with BrOMe to obtain the desired product 4b. The (R, R) diastereomer can be achieved by coupling intermediate 2b with compound namely trans-(5R,6R) 5-bromo-6-methoxy-5,6 dihydro-3'-azido-3'-deoxythymidine.

The nucleosides used as spermicidal active agents in the present invention can be formulated into contraceptive compositions for use. Such compositions are intended particularly for use with mammals, i.e. any class of higher vertebrates that nourish their young with milk secreted from mammary glands, for example humans, rabbits and monkeys. It is expected that the present invention will be used by humans in most practical applications.

The contraceptive compositions of the present invention contain one or more of the spermicidal nucleosides. The total amount of spermicide will typically range from about 0.025 to 0.5 weight percent based on the total weight of the contraceptive composition. The amount of spermicide employed generally will be that amount necessary to achieve the desired spermicidal and anti-viral protective results. The amounts can be varied as needed for specific compositions. Preferably, the amount of the spermicidal AZT derivative employed will be from about 0.05 to 0.5 weight percent, and more preferably from about 0.05 to 0.25 weight percent, based on the total weight of the contraceptive composition.

The contraceptive compositions of the present invention contain not only the spermicidal nucleoside, but also pharmaceutically acceptable carriers, diluents or vehicles as needed, i.e., materials for appropriately delivering and/or maintaining the spermicidal nucleosides to a site for contact with sperm and so as to provide the desired spermicidal and anti-viral protective activity.

One advantageous component in the pharmaceutical composition for administration of a spermicide is a polymeric delivery component as described in U.S. Pat. No. 5,595,980, which patent is incorporated herein by reference. It has been found that such polymeric delivery component enhances the effectiveness of a spermicide and reduces vaginal irritation on administration.

In addition to the polymeric component, the balance of the contraceptive compositions, i.e., typically from about 0.1 to 99.8% and often about 50 to 99.8 weight percent, may optionally comprise one or more cosmetic ingredients. Such cosmetic ingredients are known to those skilled in the art and are often referred to in the art as diluents, solvents and adjuvants. Typically cosmetic ingredients include, for example; water, ethyl alcohol, isopropyl alcohol, glycerin, glycerol propylene glycol, sorbitol and other high molecular weight alcohols. In addition, contraceptive compositions may contain minor amounts, e.g. from about 0.1 to 5% weight based on the weight of the contraceptive compositions, of other additives, such as, for example; stabilizers, surfactants, menthol, eucalyptus oil, other essential oils, fragrances, and the like. Polyoxyethylene 20 sorbitan monolaurate is a preferred stabilizer for use in the compositions. The selection and amounts of cosmetic ingredients, other additives, and blending procedures can be carried out in accordance with techniques well-known in the art.

The spermicidal active ingredients, and contraceptive compositions containing the same, of the present invention may be delivered to the vagina of a mammal by any means known to those skilled in the art. Typical forms for delivery of the compositions include, for example; creams, lotions, gels, foams, intervaginal devices such as sponges and suppositories, and films. In addition, the contraceptive compounds and compositions of the present invention may be used as personal care products, such as, for example, condom lubricants, and the like. Such lubricants may comprise commonly known ingredients such as, for example: humectants; e.g., glycerin, sorbitol, mannitol, glycols and glycol ethers; buffers, e.g., glucono-d-lactone; germicides or bactericides; e.g., chlorhexidine gluconate; preservatives, e.g., methylparaben; viscosifiers; e.g., hydroxyethyl cellulose, etc.; other adjuvants; e.g., colors and fragrances; in addition to the compositions of the present invention. Those skilled in the art will recognize that the physical properties, e.g., viscosity, of such delivery forms may vary widely. For example, the viscosity of a gel form of the composition of the present invention, e.g., 150,000 centipoise, may be substantially higher than the viscosity of lotion form of the composition of the present invention, e.g., 100 centipoise. Further details concerning the materials, ingredients, proportions and procedures of such delivery forms can be selected in accordance with techniques well-known in the art.

The contraceptive compositions of the present invention are preferably administered to the vagina of the mammal in a dosage which is effective to immobilize sperm present in the vagina and/or to inhibit their penetration in cervical mucus. Typical dosages range between about 0.0001 to 0.001 grams of the composition per kilogram of body weight of the mammal.

Intervaginal devices also may be used to aid in the administration of the spermicidal active ingredients or contraceptive compositions containing the same as described in U.S. Pat. No. 5,069,906, the disclosure of which is incorporated herein by reference.

In administering the spermical active ingredients in the form of the above compositions, the compositions also may be formulated to release the spermicide both rapidly and with a prolonged release of the drug. Such a formulation providing both rapid and prolonged release has been described in U.S. Pat. No. 4,707,362, which also is incorporated herein by reference.

The invention will be explained further with reference to the following examples, which should not be considered to limit the invention.

EXAMPLES

The effect of AZT derivatives of the present invention was evaluated. Several AZT derivatives were prepared in accordance with the synthesis techniques discussed above. The specific derivatives are shown in Tables 1 and 2 below.

Synthetic Examples

5-Bromo-6-methoxy-5,6-dihydro-3'-amino-3'-deoxythymidine

A freshly prepared solution of methyl hypobromite (bromine in anhydrous methanol) was added dropwise into a solution of 3'-amino-3'-deoxythymidine (0.10 g, 0.41 mmol) in anhydrous methanol (5 mL) with stirring until the light yellow color of the reaction mixture persisted. The reaction was allowed to proceed for 20 minutes. Removal of the solvent in vacuo afforded 5-bromo-6-methoxy-5,6-dihydro-3'-amino-3'-deoxythymidine (0.2 g, 100%) and as yellow foam solids; m.pt. 188–190° C. (d), UV (MeOH): $\lambda_{max}$ 202,235 nm. IR(KBr) : 3440, 2979, 2358, 2107, 1699, 1469, 1249 and 1085 Cm$^{-1}$. $^1$H NMR (DMSO) δ 8.25 (s, 1H, NHC=O), 6.20 (dd, J=8.0, 5.9 Hz, 1H, H-1'), 5.08 (s, 1H, H-6), 3.99 (m, 1H, H-3'), 3.69 (br s, 2H, NH$_2$), 3.40 (s, 2H, H-5'), 3.21 (s, 3H, CH$_3$O), 2.49–2.15 (m, 2H, CH$_2$-2'), 1.83 (s, 3H, CH$_3$).MS (CI, m/e) 353.9(M+1, 23), 351.6 (21), 339.8(4), 338 (5), 321.8 (10), 319.8(13), 304.8 (1), 230(1).

(5R,6R)-5-Bromo-6-(d3)methoxy-5,6-dihydro-3'-azido-3'-deoxythymidine

A freshly prepared solution of deuterated methyl hypobromite (bromine in deuterated methanol) was added dropwise into a solution of AZT (0.50 g, 1.87 mmol) in deuterated methanol (5 mL) with stirring until the light yellow color of the reaction mixture persisted. The reaction was allowed to proceed for 20 minutes. Removal of the solvent in vacuo and application of the residue to preparative thin-layer chromatography (PTLC) afforded both (5R,6R)-5-bromo-6-(d3)methoxy-5,6-dihydro-3'-amino-3'-deoxythymidine (0.791 g, 44%) and (5S,6S)-5-bromo-6-(d3)methoxy-5,6-dihydro-3'-amino-3'-deoxythymidine (0.527 g, 28%) as white foam solids; UV (MeOH): $\lambda_{max}$, 237, 305 nm. IR (Neat liquid,KBr disc): 3396, 3097, 2942, 2836, 2096, 1712, 1459, 1380, 1247, 1080 Cm$^{-1}$ $^1$H NMR (CDCl$_3$) (5R,6R) δ 1.95 (s, CH$_3$), 2.2 (m), 2.85 (q), 3.7–3.78 (dd), 4.2–4.44 (m), 4.90 (s), 5.90 (t), 8.6 (bs, NH); $^{13}$C NMR (CDCl$_3$):δ 22.82 (CH$_3$), 36.98 (C-2'), 53.15 (C-5), 57.53 (OCH$_3$), 60.02 (C-3'), 61.97 (C-5'), 83.94 (C-4'),86.36 (C-1'), 89.10 (C-6), 150.65 (C-2,CO), 167.33 (C-4,CO). GC/MS: M+NH$_3$, 398 (100.0), M+2, 383, (62.0), M+1, 382 (9.9), M$^+$, 381 (65.5), 365 (8.0), 363 (8.0), 348 (61.0), 346 (62.0), 287 (4.9), 285 (10.5), 268 (23.6), 211 (6.8), 159 (6.8), 127 (7.8), 116 (8.7), 114 (17.8), 99 (26.7), 89.1 (12.6), 86.1 (9.6), 35 (4.5).

5-Bromo-6-methoxy-5,6-dihydro-3'-azidothymidine-5'-(p-Methoxyphenyl Methoxyalaninyl Phosphate):

A freshly prepared solution of methyl hypobromite (bromine in anhydrous methanol) was added dropwise into a solution of 3'-azidothymidine 5'-(p-methoxyphenyl methoxyalaninyl phosphate) (0.11 g, 0.2 mmol) in anhydrous methanol (5 mL) with stirring until the light yellow color of the reaction mixture persisted. The reaction was allowed to proceed for 20 min. Removal of the solvent in vacuo and application of this material to the top of a silica gel column followed by elution with chloroform-methanol (95:5, v/v) afforded 5-bromo-6-methoxy-5,6-dihydro-3'-azidothymidine 5'-(p-methoxyphenyl methoxyalaninyl phosphate) (0.085 g, 0.13 mmol, 64%) as a yellow viscous oil; UV (MeOH) $\lambda_{max}$ 329, 280, 241 nm. IR (neat in KBr disc): 3282, 2954, 2838, 2358, 2103, 1739, 1635, 1506, 1456, 1378, 1209, 1103 Cm$^{-1}$. $^1$H NMR (CDCl$_3$) δ 7.66 (s, 1H, NHC=O), 7.26–7.10 (m, 2H, o-H), 6.87–6.76 (m, 2H, m-H), 6.04 (d, J=6.2,2.3 Hz, 1H, H-1'), 4.88 (s, 1H, H-6), 4.33–4.22 (m, 1H, H-3'), 4.07–3.98 (m, 3H, H-4', 5'), 3.77 (s, 3H, CH$_3$OPh), 3.72 (s, 3H, CH$_3$OC=O), 3.48 (s, 3H, CH$_3$O-6), 3.44 (d, J=3.5 Hz, 1H, NH), 2.46–2.31 (m, 2H, CH$_2$-2'), 1.96 (s, 3H, CH$_3$-5), 1.36 (d, J=6.8 Hz, 3H, CH$_3$-Ala). $^{13}$C NMR (CDCl$_3$) δ 173.7 (COOMe), 167.30 (C2), 156.6 (Ph para), 150.7 (C4), 149.0(Ph ipso), 121.6 (Ph ortho), 114.6(Ph meta), 87.4(C6), 84.7 (C1'), 81.44 (C4'), 61.3 (C5'), 60.1(C3'), 57.9(OMe), 55.6 (Ph OMe), 52.5 (C5), 52.4 (COOMe), 50.5 (Ala CH), 36.61 (C2'), 22.74 (Me), 20.93 (Ala Me). Additional peaks were observed for the isomers as shown below: 150.2, 120.8, 114.44), 93.3, 89.82, 65.3, 65.6, 65.9, 56.9, 55.58, 50.37, 35.2 etc., $^{31}$P NMR (CDCl$_3$) δ: 3.51 & 3.38 ppm, relative to phosphoric acid as standard at 0 ppm. MS/Electron spray: 651, 649 (M+1). GC/mass: 645 (0.2), 643 (2.3), 572 (0.8), 559 (20.4), 558 (100), 501 (2.3), 446 (4.6), 435(3.5), 416 (1.4), 409 (7.9), 328 (2.7), 272(6.1), 245 (1.6), 244 (8.8), 204 (3.2), 200 (0.1), 139 (6.1), 138 (4.7), 126 (10.1), 124 (29.0), 123 (3.3), 109 (14.01), 91 (11.5), 81 (11.9), 77 (13.1), 60 (13.6), 55 (9.0), 44 (26.2), 43 (54.9).

p-Bromophenyl Phosphorodichloridate.

A solution of p-Bromophenol and triethylamine in anhydrous diethyl ether was added dropwise to a vigorously stirred solution of phosphoryl chloride in diethyl ether at 0° C. The mixture was allowed to warm to ambient temperature, with stirring for 15 hours, and then heated under reflux for 2 hours. The mixture was filtered, and the precipitate was washed with diethyl ether. The combined filtrate and washings were evaporated to dryness under reduced pressure to yield a colored oil. The oil was subjected to vacuum distillation to give the product as a colorless oil; B.Pt 97° C./0.1 mm, Yield 90%, UV (MeOH) $\lambda_{max}$ 271, 242 nm, IR (KBr disc) 3878, 3095, 2358, 1888, 1712, 1483, 1189, 831 Cm$^{-1}$, $^1$H NMR(CDCl$_3$) δ 7.50 (d, 2H, aryl H, J=9.0 Hz), 7.15 (d, 2H, aryl H, J=9.0 Hz, $^{13}$CNMR(CDCl$_3$) δ: 148.5, 133.30, 122.38, 120.48. $^{31}$P NMR (CDCl$_3$.) δ 3.12.

p-Bromophenyl Methoxyalaninyl Phosphorochloridate.

A solution of triethylamine in anhydrous dichloromethane was added dropwise with vigorous stirring to a solution of L-alanine methyl ester hydrochloride and p-bromophenyl phosphorodichloridate in dichloromethane at −70° C. The reaction mixture was slowly warmed to ambient temperature with stirring over 6 hours, and the solvent was then removed in vacuo. The residue was treated with diethyl ether, the mixture was filtered, and the filtrate was concentrated to give the product as a colorless Viscous oil; Yield 80%, UV (MeOH): $\lambda_{max}$ 272, 231, $^1$H NMR (CDCl$_3$) δ 8.70 (s, br, 1H, Ala-NH), 7.16 (d, 2H, aryl H, J=9.0 Hz), 7.48 (d, 2H, aryl H,J=9.0 Hz), 3.793 (s, 1H, —OCH$_3$), 3.77 (s, 1H, —OCH$_3$), 1.51 (d, 3H, Ala-CH$_3$), 1.40 (d, 3H, Ala-CH$_3$); $^{13}$C NMR (CDCl$_3$) δ: 172.78&172.54, 148.46&148.50, 132.61&132.49, 122.14& 122.05, 52.70 &52.60, 50.31 & 50.51, 20.20 & 20.11 (two isomers). $^{31}$P NMR (CDCl$_3$) δ: 8.48& 8.35. IR (neat): 3212 (s, br), 2989 & 2952 (w-m), 1747 (s), 1483 (s), 1270, 1209 & 1147 (s), 1010 & 927 1(s), 831 (m), 757 (m) cm$^{-1}$; MS (CI, m/e): 357.9 (M$^+$+2), 355.9 (M$^+$), 322.0 (M$^+$+2-Cl), 320 (M$^+$—Cl), 295.9 (M$^+$—COOCH$_3$), 186.0(M$^+$+2-Br—Ph—O), 184.0 (M$^+$—Br—Ph—O).

3'-Azidothymidine 5'-(p-Bromophenyl Methoxyalaninyl Phosphate)

AZT was dissolved in THF, and p-bromophenyl methoxyalaninyl phosphorochloridate and N-methylimidazole was added with vigorous stirring. After 12 hours at ambient temperature the solvent was removed under vacuum. The residue was dissolved in chloroform and washed with 1 M hydrochloric acid, saturated sodium bicarbonate solution, and then water. The organic phase was dried and evaporated under vacuum, and the residue was purified by chromatography on silica gel by elution with 5% methanol in chloroform. Concentration led to the desired product; Yield 83%. $^1$H NMR (CDCl$_3$) δ 8.69 (s, br, 1H, 3-NH), 7.45 (d, 2H, aryl H, J=9.0 Hz), 7.33 (s, 1H, vinyl H at C6), 7.11 (d, 2H, aryl H, J=9.0 Hz), 6.18 (t, 1H, J=6.6 Hz, H at C1) 6.13 (t, 1H, J=6.6 Hz, H at C1), 4.44–3.77 (m, 6H, H's at C3', 4', 5', Ala-NH and Ala-CH), 3.73 (s, 3H, —COOCH$_3$), 3.72 (s, 3H, —COOCH$_3$), 2.18 (s, 3H, —CH$_3$ at C5), 1.90 (s, br, 3H, Ala-CH$_3$). $^{13}$C NMR (CDCl$_3$) δ: 173.6 (COOMe, weak), 163.2,160.7 (C2, weak), 149.9 (C4),144.1,144.35(d, Ph ipso, J=6 Hz), 135.4(C6), 121.79,121.72 (m,Ph ortho),119 (Ph meta), 111.36 (C5), 85.41,85.05 (C1'), 82.20(C4'), 65.73 (C5'), 60.31, 60.17 (C3'), 52.75 (Ala OMe), 50.37, 50.22 (Ala CH), 37.28 (C2'), 21.07 (Ala Me), 12.54 (C5-Me). IR (KBr): 3205 (m, br), 3066 (w), 2954 9w), 2109 (s), 1475 (s), 1691 (vs), 1484 (m), 1270 & 1216 (m), 1153 (w-m), 1010 &926 (m), 833 &757 (w)cm$^{-1}$. MS (CI, m/e): 589.1 (M$^+$+2), 587.1 (M$^+$), 418.0 (M$^+$+2-Br—Ph—O), 416.0 (M$^+$—Br—Ph—O), 340.0 [M$^+$+2-(AZT-O)], 338.0 [M$^+$-(AZT-O)], 250.1 [(AZT-O)$^+$], 81 (Br).

5-Bromo-6-methoxy-5,6-dihydro-3 '-azidothymidine-5'-(p-Bromophenyl Methoxyalaninyl Phosphate).

A freshly prepared solution of methyl hypobromite (bromine in anhydrous methanol) was added dropwise into a solution of 3'-azidothymidine 5'-(p-bromophenyl methoxyalaninyl phosphate) in anhydrous methanol (5 mL) with stirring until the light yellow color of the reaction mixture persisted. The reaction was allowed to proceed for 20 minutes. Removal of the solvent in vacuo and application of this material to the top of a silica gel column followed by elution with chloroform-methanol (95:5, v/v) afforded 5-bromo-6-methoxy-5,6-dihydro-3'-azidothymidine 5'-(p-bromophenyl methoxyalaninyl phosphate) as a yellow viscous oil; Yield 73%. IR (Neat,KBr Disc):3218, 3093, 2925, 2850, 2105.9, 1712, 1484, 1456, 1378, 1241, 1153, 1010, 929 Cm$^{-1}$. $^1$H NMR (CDCl$_3$) δ 7.70 (br s, 1H, 3-NH), 7.43 (2H, d, Aryl H, J=9.0 Hz), 6.01 (1H, t, —CH at C-1'), 4.87(1H, s, —CH at C-6), 4.35–3.96 (6H, m, —CH at C-3', 4', 5' & Ala-NH, a —CH), 3.74 (3H, s, —COOCH$_3$), 3.44 (3H, s, —OCH$_3$ at C-6), 2.56–2.47 & 2.41–2.30 (1H & 1H, m & m, —CH at C-2'), 1.93 (3H, s, —CH$_3$ at C-5), 1.39 & 1.37 (3H, d, a —CH$_3$ of Ala); $^{13}$C NMR (CDCl$_3$) δ: 173.6(COOMe), 166.7 (C2), 150.1 (C4), 148.9 (d,Ph ipso), 132.7&132.5 (C6), 121.9 (Ph, ortho), 121.7 (Ph, meta), 85.14 (C1'), 81.46 & 81.57&81.7(m,C4'), 65.48&65.60 (m,C5'), 60.0(C3'), 57.9&57.8(C5), 52.77 (al Ome), 50.25&50.37 (Ala CH), 36.96 & 36.91 (C2'), 22.87 &22.77 (Me), 21.13 &21.19 (d, Ala Me) (double peaks are due to several isomers) $^{31}$P NMR (CDCl$_3$, Phosphoric acid as internal reference at 0 ppm) δ: 2.854, 2.754 (1:1) & 2.7 & 2.46 (3:1) due to four isomers present in the system. MS (CI, m/e): 700.5 (M$^+$+4), 698.5 (M$^+$+2), 696.5 (M$^+$), 588.8 (M$^+$+2-Br—OCH$_3$), 586.8 (M$^+$—Br—OCH$_3$).MALDI-TOF 721.8 (M$^+$+Na).

Physical Data of Other Synthesized Compounds (5S,6S)-5-Bromo-6-(d3)-methoxy-5,6-dihydro-3'-azidothymidine $^1$H NMR (CDCl$_3$) δ 8.00 (br s, 1H), 5.28–5.20 (t, 1H), 4.58 (s, 1H), 4.52–4.48 (m, 2H), 3.75–3.70 (dd, 1H), 2.90 (q, 1H), 2.20 (m, 2H), 2.00 (s, 3H); GC/mass: 383 (M+2, 97.0), 382 (M+1, 13.0), 381 (M$^+$, 100), 377 (5.0), 365 (6.0), 363 (6.0), 351 (4.0), 349 (3.0), 348 (45.0), 347 (5.0), 346 (41.0), 310 (22.0), 309 (2.0), 308 (21.0), 268 (23.0), 267 (9.0), 186 (4.0), 159 (4.0), 127 (10.0), 116 (5.0), 115 (1.0), 114 (7.0), 102 (7.0), 99 (4.0), 89 (15.0), 81 (6.0); UV (MeOH): λ$_{max}$ 237 and 305 nm; IR (neat): 3396, 3097, 2942, 2836, 2096, 1712 cm$^{-1}$.

trans-(5R,6R)-5-Bromo-6-methoxy-5,6-dihydro-3'-azidothymidine 5'-[p-Bromophenyl methoxyalaninyl phosphate] (WHI-07a)

Pale yellow viscous oil; yield (73%); $^1$H NMR (CDCl$_3$) δ 7.75 (br s, 1H), 7.44 (d, 2H), 7.14 (d, 2H), 6.03 (t, 1H), 4.87 (s, 1H), 4.22–4.37, 3.93–4.08, 3.62–3.78 (m, 6H), 3.74 (s, 3H), 3.44 (s, 3H), 2.31–2.58 (m, 2H), 1.93 (s, 3H), 1.38 (d, 3H); $^{13}$C NMR (CDCl$_3$) δ 174.0, 167.1, 150.6, 133.2, 122.2, 122.1, 88.2, 85.6, 81.9, 65.9, 60.4, 58.3, 54.1, 53.2, 50.7, 37.3, 23.3, 21.6; MS (MALDI-TOF) m/z 721.5 (M+Na); HPLC retention time 14.4 minutes; UV (MeOH): λ$_{max}$ 217, 226 and 270 nm; IR (Neat): 3218, 3093, 2850, 2106, 1712 cm$^{-1}$.

trans-(5S,6S)-5-Bromo-6-methoxy-5,6-dihydro-3'-azidothymidine-5'-[p-Bromophenyl methoxyalaninyl phosphate] (WHI-07b)

Colorless viscous oil; yield (42%); $^1$H NMR (CDCl$_3$ ) δ 8.37 (br, 1H), 7.44 (dd, 2H), 7.13 (d, 2H), 5.34 (t, 1H,), 5.01 (s, 1H), 3.92–4.54 (m, 6H), 3.73 (s, 3H), 3.43 (s, 3H), 2.77–2.90 (m, 1H), 2.25–2.37 (m, 1H), 1.93 (s, 3H), 1.38 (dd, 3H); $^{13}$C NMR (CDCl$_3$) δ 176.0, 166.7, 149.6, 132.5, 122.9, 94.2, 82.38, 66.2, 61.4, 57.1, 53.3, 52.6, 50.2, 35.4, 29.8, 22.8, 21.1; UV: (MeOH): λ$_{max}$ 217, 226 and270 nm; IR (Neat): 3218, 3093, 2850, 2106, 1712 cm$^{-1}$.

5-Bromo-6-methoxy-5,6-dihydro-3'-azidothymidine-5'-[p-Fluorophenyl methoxyalaninyl phosphate] (WHI-06)

Viscous liquid; yield (71%); $^1$H NMR (CDCl$_3$) δ 8.41, 8.21 (br s, 1H), 7.19 (dd, 2H), 7.03 (dd, 2H), 6.13 (t, 0.7H, 5R, 6R isomer), 5.38 (m, 0.3H, 5S, 6S isomer), 4.88 & 4.61 (d&d, 0.7H & 0.3H), 4.46–3.80 (m, 6H), 3.7 & 3.71 (s, 3H), 3.49 & 3.44 (s, 3H), 2.83–2.22 (m, 2H), 1.95 (s, 3H), 1.36 (dd, 3H); MS (MALDI-TOF) m/z 660.1 (M+Na); IR (neat): 3230, 3081, 2107, 1736, 1712, 1504, cm$^{-1}$.

trans-(5R,6R)-5-Bromo-6-ethoxy-5,6-dihydro-3'-azidothymidine 5'-[p-Methoxyphenyl methoxyalaninyl phosphate]

Viscous oil; yield (40%); $^1$HNMR (CDCl$_3$) δ 8.20 (br s, 1H), 7.15–7.11 (d, 2H), 6.86–6.82 (d, 2H), 6.10 (t, 3H), 4.94 (s, 1H), 4.33–4.00 (m, 6H), 4.03–4.02 (m, 2H), 3.80 (m, 3H), 3.70 (m, 3H), 2.50–2.40 (m, 1H), 2.40–2.20 (m, 1H), 1.92(s, 3H), 1.39–1.38 (d, 3H), 1.36 (t, 3H); $^{13}$C NMR (CDCl$_3$) δ 180.1, 166.9, 150.3, 148.1, 121.1, 121.0, 120.8, 114.6, 114.5, 114.5, 86.3, 84.9, 81.7, 81.5, 66.3, 66.2, 65.5, 65.3, 60.1, 55.9, 52.6, 52.4, 50.4, 50.2, 36.9, 22.93, 22.9, 21.2, 15.2; MS (MALDI-TOF) m/z 687.9 (M+Na); HPLC retention time 1.74 &1.82 minutes; UV (MeOH): λ$_{max}$ 208, 221, 278 nm; IR (neat): 3242, 2852, 2106, 1732, 1506 cm$^{-1}$.

trans-(5R,6R)-5-Bromo-6-ethoxy-5,6-dihydro-3'-azidothymidine

Yield (60%); $^1$HNMR (CDCl$_3$) δ 7.70 (s, 1H), 5.82 (t, 1H), 4.98 (s, 1H), 4.40–4.30 (m, 1H), 4.00–3.72 (m, 4H), 3.60–3.50 (m, 1H), 2.77–2.68 (q, 1H), 2.37–2.29 (dd, 1H), 1.97 (s, 3H), 1.17 (t, 3H); MS (MALDI-TOF) m/z 415.7 (M+Na); UV (MeOH): λ$_{max}$ 210 and 214 nm; IR (neat): 3485, 3217, 3093, 2104, 1685 cm$^{-1}$.

trans-(5S,6S)-5-Bromo-6-ethoxy-5,6-dihydro-3'-azidothymidine

Viscous oil; yield (24%); $^1$HNMR (CDCl$_3$) δ 7.40 (s, 1H), 5.22 (t, 1H), 4.60 (s, 1H), 4.02–3.68 (m, 4H) 3.60–3.50 (m, 1H), 2.98 (q, 1H), 2.22 (dd, 1H), 1.97 (s, 3H), 1.25–1.22 (t, 3H); MS (MALDI-TOF) m/z 415.7 (M+Na); UV (MeOH): λ$_{max}$ 210 and 214 nm; IR (neat): 3485, 3217, 3093, 2929, 2104, 1685 cm$^{-1}$.

5-Bromo-6-methoxy-5,6-dihydro-3'-deoxythymidine 5'-[p-Methoxyphenyl methoxyalaninyl phosphate]

Viscous oil; yield (86%); $^1$HNMR (CDCl$_3$) δ 8.24 (br s, 1H), 7.36–7.26 (m, 2H), 6.94–6.92 (m, 2H), 6.03–5.99 (m, 1H), 5.1–5.0 (s, 1H); 4.40–4.0 (m, 5H), 3.87–3.86 (s, 3H), 3.80–3.79 (s, 3H), 3.55–3.54 (m, 3H), 2.34–2.03 (m, 7H), 1.46–1.43 (d, 3H); $^{13}$C NMR (CDCl$_3$) δ 173.7, 167.9, 156.3, 150.3*, 143.7*, 120.7*, 114.3*, 86.7, 86.2*, 78.4*, 67.6*, 57.8*, 55.6, 52.4*, 50.1*, 31.8*, 25.7*, 22.8, 21.1; $^{31}$P NMR (CDCl$_3$) δ 3.11, 3.22 (1:1); MS (MALDI-TOF) m/z 631.8 (M+Na); HPLC retention time 14.54, 15.18 minutes; UV (MeOH): λ$_{max}$ 226 and 279 nm; IR (neat): 3419, 2850, 1645, 1506 cm$^{-1}$.

trans-(5R,6R)-5-Bromo-6-methoxy-5,6-dihydro-3'-azidothymidine 5'-[o,o-Dimethoxyphenyl methoxyalaninyl phosphate]

Colourless viscous liquid; $^1$H NMR (CDCl$_3$) δ 7.44 (s, 1H), 7.05 (t, 1H), 6.59 (d, 1H), 6.12* (t, 1H), 5.90* (t, 1H), 4.98 (s, 1H), 4.5–4.3 (m, 1H), 4.20–4.05 (m, 1H), 3.88* (s, 3H), 3.86* (s, 3H), 3.90–3.84 (m, 2H), 3.74* (s, 3H), 3.73* (s, 3H), 3.73 (q, 1H), 3.48 (s, 6H), 2.70–2.30 (m, 2H), 1.97 (s, 3H), 1.43* (d, 3H), 1.38* (d, 3H); $^{13}$C NMR (CDCl$_3$) δ 151.9, 137.5, 129.1, 125.3, 124.9, 124.7, 88.2, 87.1, 85.8, 84.4*, 84.3*, 84.1, 81.8*, 81.7*, 61.7, 60.1, 56.1, 49.8, 37.0*, 36.8*, 22.9, 21.3, 21.2; $^{31}$P NMR (CDCl$_3$) δ 5.70, 5.27; MS (MALDI-TOF) m/z 702.4 (M+Na); IR (neat): 3340 (br), 2096, 1741, 1710 cm$^{-1}$.

(5S,6S)-5-Bromo-6-methoxy-5,6-dihydrothymidine

White foam, yield (20%); 1H NMR (DMSO-d$_6$) δ 10.87 (s, 1H), 5.76 (t, J=6.3 Hz, 1H), 5.18 (s, 1H), 5.17 (s, 1H), 4.80 (s, 1H), 4.24 (m, 1H), 3.72 (m, 1H,), 3.52 (m, 1H), 3.44 (s, 3H), 2.2 (m, 1H), 2.0 (m, 1H), 1.84 (s, 3H); $^{13}$C NMR (DMSO-d$_6$) δ 167.9, 150.4, 88.9, 86.9, 86.7, 71.1, 62.2, 57.3, 53.8, 37.7, 22.7; MS (MALDI-TOF) m/z 375.3 (M+Na), 377.3 (M+2+Na); IR (neat): 3371 (br), 3214 (shoulder), 1706 cm$^{-1}$.

(5R,6R)-5-Bromo-6-methoxy-5,6-dihydrothymidine

White foam; yield (80%); $^1$H NMR (DMSO-d$_6$) δ 10.84 (br s, 1H), 6.04 (dd, 1H, J=8.4, 5.4 Hz), 5.18 (s, 1H), 5.13 (s, 1H), 4.89 (s, 1H), 4.18 (m, 1H), 3.74 (m, 1H), 3.53 (m, 1H), 3.42 (s, 3H), 2.20 (m, 1H), 1.80 (m, 1H), 1.84 (s, 3H); $^{13}$C NMR (DMSO-d$_6$) δ 167.9, 150.9, 86.7, 86.2, 83.4, 70.5, 61.8, 57.9, 54.5, 38.2, 22.6; MS (MALDI-TOF) m/z 375.8 (M+Na) & 377.4 (M+2+Na); IR (neat): 3366 (br), 3214 (shoulder), 1701 cm$^{-1}$.

5-Bromo-6-methoxy-5,6-dihydro-3'-deoxythymidine 5'-[p-Bromo phenyl methoxyalaninyl phosphate] (WHI-11)

Viscous oil; yield (86%); $^1$H NMR (CDCl$_3$) δ 8.74 (br s, 1H), 7.46–7.44 (m, 2H), 7.16–7.10 (m, 2H), 5.91 (t, 1H), 5.1–5.0 (s, 1H), 4.40–4.0 (m, 5H), 3.79* (s, 3H), 3.54* (s, 3H), 2.29–1.93 (m, 7H), 1.39–1.37 (d, 3H); $^{13}$C NMR (CDCl$_3$) δ 173.5, 167.1, 150.5, 148.5* 132.5*, 121.9*, 117.7, 86.8, 86.2*, 78.3*, 67.6*, 57.8*, 53.8*, 50.1*, 31.6*, 25.7*, 22.8*, and 20.9*; $^{31}$P NMR (CDCl$_3$) δ 2.65 and 2.74 (1:1), MS (MALDI-TOF) m/z 679.1 (M–1+Na); HPLC retention time 23.87, 24.49 minutes; UV (MeOH): λ$_{max}$ 226 and 274 nm; IR (neat): 3417, 1705, 1614 cm$^{-1}$.

3'-Amino-3'-deoxythymidine 5'-[p-Methoxyphenyl methoxyalaninyl phosphate]

Colourless liquid; yield(70%); $^1$H NMR (CDCl$_3$) δ 7.44 (br d, 1H), 7.15–7.10 (d, 2H), 6.82–6.80 (d, 2H), 6.28–6.20 (t, 1H), 4.42–3.80 (m, 6H), 3.75 (s, 3H), 3.71 (s, 3H,), 2.40–2.28 (m, 2H), 1.88 (br s, 3H), 1.39 &1.35 (dd, 3H); $^{13}$C NMR (CDCl$_3$) δ 173.8, 163.8, 156.4, 150.3, 135.2, 121.0, 120.8, 114.4, 113.8, 110.8, 84.9, 84.2, 66.0, 58.0, 55.5, 55.3, 51.1, 34.2, 21.1, 20.8, 20.1; MS (MALDI-TOF) m/z 535.5 (M+Na); HPLC retention time 10.48, 10.49 minutes; UV (MeOH): λ$_{max}$ 218, 225 and 273 nm; IR (Neat): 3261, 2839, 2096, 1741, 1693, 1506 cm$^{-1}$.

5-Bromo-6-methoxy-5,6-dihydro-3'-azidothymidine 5'-[Phenyl methoxyalaninyl phosphate] (WHI-04)

Viscous oil; yield (92%); $^1$HNMR (CDCl$_3$) δ 7.90 (br s, 1H), 7.37–7.15 (m, 5H), 6.06–6.02 (t, 1H), 4.87* (s, 1H), 4.40–4.0 (m, 5H), 3.72 (s, 3H), 3.44* (s, 3H), 2.29–1.93 (m, 6H), 1.39–1.37 (d&d, 3H); $^{13}$C NMR (CDCl$_3$) δ 173.5, 167.1, 152.1*,150.5, 129.8*, 125.2*, 120.1*, 87.3, 84.7, 81.5, 60.0, 57.9*, 52.6*, 50.1*, 36.7, 35.2, 22.7, 21.0; $^{31}$P NMR (CDCl$_3$) δ 2.32, 2.51 (minor peaks) and 2.58, 2.71 (major peaks) (1:1); MS (MALDI-TOF) m/z 679.1 (M–1+Na); HPLC retention time 17.60, 20.90 minutes; UV (MeOH): λ$_{max}$ 218 and 262 nm; IR (neat): 3265, 2852, 2104, 1713, 1591 cm$^{-1}$.

5-Bromo-6-methoxy-5,6-dihydro-3'-deoxythymidine 5'-[Phenyl methoxyalaninyl phosphate] (WHI-12)

Viscous oil; yield (86%); $^1$H NMR (CDCl$_3$) δ 7.94 (br s, 1H), 7.46–7.10 (m, 5H), 5.93–5.90 (t, 1H), 5.02* (s, 1H), 4.40–4.0 (m, 5H), 3.70* (s, 3H), 3.45* (s, 3H), 2.29–1.93 (m, 7H), 1.39–1.37 (d&d, 3H); $^{13}$C NMR (CDCl$_3$) δ 173.5, 167.2, 150.5*, 129.8, 129.5*, 125.0, 120.0, 86.7*, 78.4*, 67.6*, 57.9*, 53.7, 52.6, 50.1*, 31.7*, 25.6, 22.8, 21.0; $^{31}$P NMR (CDCl$_3$) δ 2.51, 2.58 (minor peaks) and 2.65, 2.74 (major peaks) (1:1); MS (MALDI-TOF) m/z 642.1 (M+Na); HPLC retention time 6.97, 7.41 minutes; UV (MeOH): λ$_{max}$: 230 and 241 nm; IR (neat): 3226, 2850, 1728, 1591 cm$^{-1}$.

Example 1

Methods

To evaluate anti-HIV-1 activity of AZT and various derivatives, normal peripheral blood mononuclear cells were cultured for 72 hours in RPMI 1640 medium (Gibco-BRL) supplemented with 20% (v/v) heat-inactivated fetal calf serum, 3% interleukin-2, 2 mM glutamine, 25 mM HEPES, 2 g/l NaHCO$_3$, 50 μg/ml gentamicin, and 4 μg/ml phytohemagglutinin prior to exposure to HIV-1 at a multiplicity of infection of 0.1 during a 1 hour adsorption period. Subsequently, cells were cultured in 96-well microtiter plates (100 μl/well; 2×10$^6$/ml, triplicate wells) in the presence and absence of various concentrations (0.00 μM to 100 μM) of drugs for 7 days. Aliquots of culture supernatants were removed from the wells on the 7th day after infection for p24 antigen enzyme immunoassay as an indication of viral replication. Erice et al. *Antimicrob. Agents and Chemother.* 37, 835 (1993); J. M. Zarling et al. *Nature* 347, 92 (1990) F. M. Uckun et al., *Antimicrob. Agents and Chemother.* 42, 383 (1998). Percent inhibition of virus replication was calculated by comparing the p24 antigen values from the test drug-treated infected cells with p24 antigen values from untreated infected cells. The anti-HIV activity of tested compounds was expressed as the IC$_{50}$ (the fmal concentration of the compound in culture medium that decreases the replication of HIV-1, by 50%). Cell viability was quantified by a calorimetric MTA assay. F. M. Uckun et al., *Antimicrob.*

Agents and Chemother. 42, 383 (1998).

To evaluate the potential toxic effects of AZT and various derivatives and to compare with the detergent spermicide nonoxynol-9 (N-9; IGEPAL CO-630; Rhone Poulenc, Cranbury, N.J.), on sperm motility, a highly motile fraction of pooled donor sperm (n=10) was prepared by discontinuous (90–45%) Percoll gradient (Conception Technologies, San Diego, Calif.) centrifugation and "swim-up" method as previously described [O. J. D'Cruz and G. G. Haas Jr., *Biol. Reprod.* 53, 1118 (1995)]. All donor specimens were obtained after informed consent and in compliance with the guidelines of the Wayne Hughes Institute Institutional Review Board. Motile sperm ($\geq 10 \times 10^6$/ml), were suspended in 0.5 ml of Biggers, Whitten, and Whittingam's medium (BWW) containing 25 mM HEPES (Irvine Scientific, Santa Ana, Calif.), and 0.3% bovine serum albumin (BSA; Fraction V, Sigma Chemical Co, St. Louis, Mo.) in the presence and absence of serial two-fold dilutions of test substance (300 μM to 4.6 μM) in 1% DMSO. The stock solutions of synthetic WHI compounds were prepared in DMSO (10 mg/ml) and diluted in DMSO to yield the desired concentrations. Corresponding volume of DMSO (1%) was added to control tubes. N-9 was diluted in BWW-0.3% BSA (pH 7.4) to yield the desired concentrations (4.6 to 300 μM). After 3 hours of incubation at 37° C., the percentage of motile sperm was evaluated by computer-assisted sperm analysis (CASA) as described [L. J. Burkman, *Fertil. Steril.* 55, 363 (1991), O. D'Cruz et al., in press, *Biol. Reprod.* 1998]. The percent motilities were compared with sham-treated control suspensions of motile sperm. The spermicidal activity of test compounds was expressed as the $EC_{50}$ (the final concentration of the compound in medium that decreases the proportion of motile sperm by 50%). Non-linear regression analyses were used to determine the $EC_{50}$ values from the concentration effect curves using GraphPad PRISM software (San Diego, Calif.).

For evaluating sperm motion kinematics using CASA, 4 μl each of sperm suspension was loaded into two 20-μm Microcell chambers (Conception Technologies) that was placed onto a counting chamber at 37° C. At least 5–8 fields per chamber were scanned for analysis using a Hamilton Thorne Integrated Visual Optical System (IVOS), version 10 instrument (Hamilton Thorne Research Inc., Danvers, Mass.). Each field was recorded for 30 seconds. The Hamilton Thorne computer calibrations were set at 30 frames at a frame rate of 30/second; microscope stage temperature maintained at 37° C. with stage warmer; minimum contrast 8; minimum size 6; low-size gate, 1.0; high-size gate, 2.9; low-intensity gate, 0.6; high-intensity gate, 1.4; phase-contrast illumination; low path velocity at 10 μM/second, and threshold straightness at 80%; HTM magnification factor, 1.95. The performance of the analyzer was periodically checked using the play-back function. The attributes of sperm kinematic parameters evaluated included numbers of motile (MOT) and progressively (PRG) motile sperm; curvilinear velocity (VCL; a measure of the total distance traveled by a given sperm during the acquisition divided by the time elapsed); average path velocity (VAP; the spatially averaged path that eliminates the wobble of the sperm head), straight line velocity (VSL; the straight-line distance from beginning to end of track divided by time taken), beat cross frequency (BCF, frequency of sperm head crossing sperm average path), the amplitude of lateral head displacement (ALH; the mean width of sperm head oscillation) and the derivatives, straightness (STR=100×VAP/VCL); linearity (LIN=100×VSL/VCL; departure of sperm track from a straight line). Data from each individual cell track were recorded and analyzed. At least 200 motile sperm were analyzed for each aliquot sampled.

Results

Figure 2:
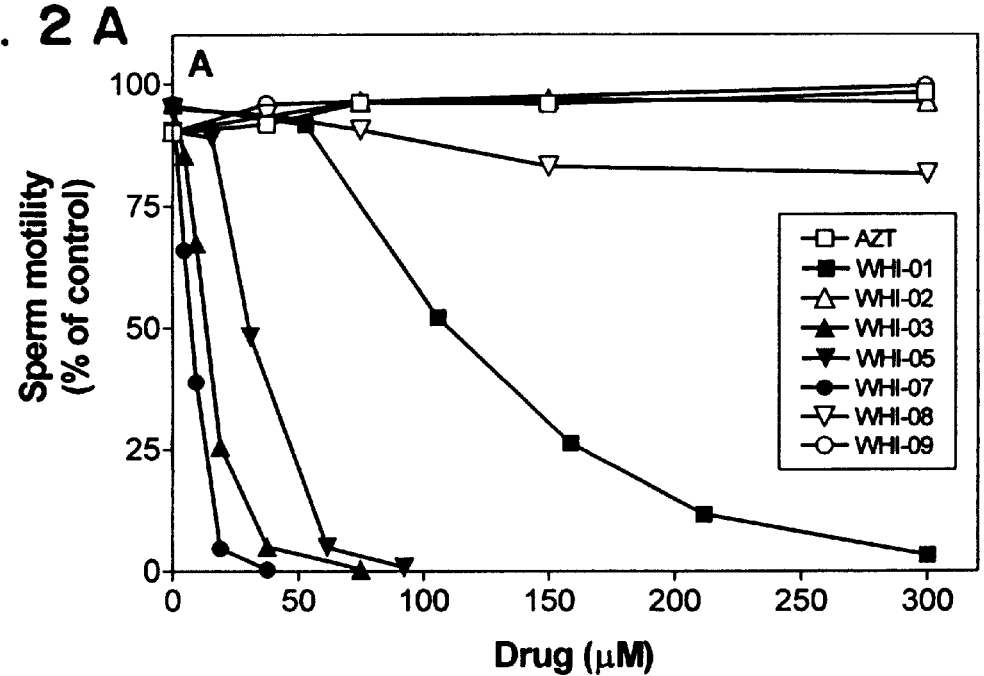
FIG. 2A shows sperm mobility as a function of concentration for AZT and various AZT derivatives of the present invention.
FIG. 2B shows progressive sperm mobility as a funtion of time for various AZT derivatives of the present invention.
Figure 2:
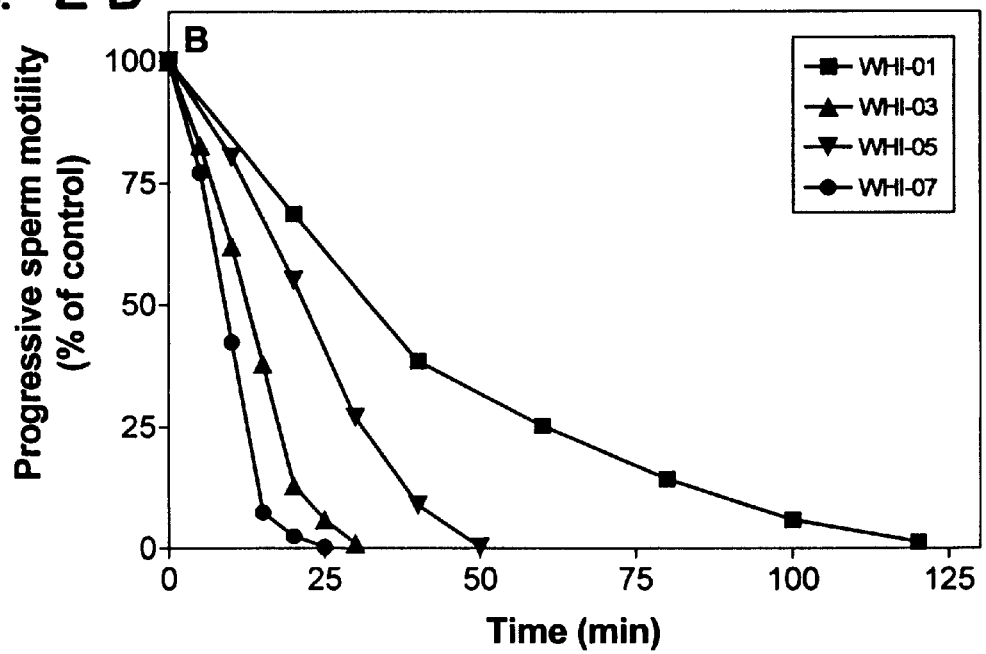

Physiological fertilization depends on the ability of the ejaculated sperm to swim, bind the zona pellucida, and penetrate the egg. These processes are primarily dependent on sperm motility. Exposure of the highly motile fraction of human sperm to AZT, which inhibited HIV-1 replication in human peripheral blood mononuclear cells in vitro with an $IC_{50}$ value of 0.006 μM, did not affect sperm motility even at concentrations as high as 300 μM (FIG. 1A). Further, sperm motion kinematics using computer-assisted sperm analysis (CASA) confirmed that AZT treatment did not alter the sperm motion parameters, such as the progressive motility, track speed, path velocity, straight line velocity, straightness of the swimming pattern, linearity of the sperm tracks, beat-cross frequency, and the amplitude of lateral sperm-head displacement. Surprisingly, introduction of a [5-bromo-6-methoxy] substituent on the thymine base ring of AZT to yield 5-bromo-6-methoxy-5,6-dihydro-AZT (compound WHI-01) resulted in gain of significant spermicidal function ($EC_{50}$=104 μM) without significantly decreasing the anti-HIV activity (FIG. 1A, FIG. 2A). Replacement of the azide group in the pentose ring with an $NH_2$ group (compound WHI-03) enhanced the spermicidal activity ($EC_{50}$=12 μM), but with a substantially reduced anti-HIV activity.

Figure 1B:
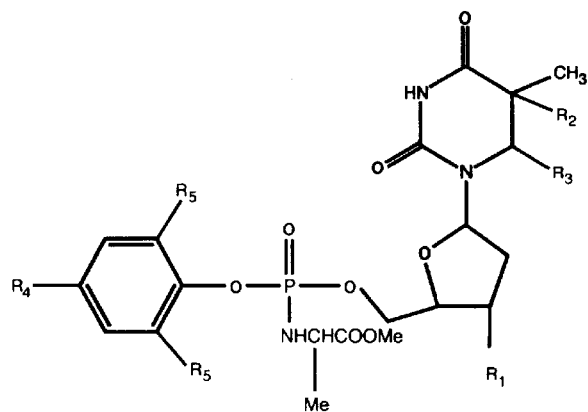
FIG. 1B compares the anti-HIV and spermicidal activity of various aryl-phosphate AZT derivatives of the present invention.

The spermicidal activity of the aryl-phosphate substituted derivatives also was evaluated by CASA (FIG. 1B). Compound WHI-04 with the unsubstituted aryl moiety exhibited improved spermicidal activity over WHI-01. Introduction of a p-methoxy (compound WHI-05, $EC_{50}$=29 μM), p-fluoro (compound WHI-06, $EC_{50}$=15 μM), or p-bromo (compound WHI-07, $EC_{50}$=6 μM) substituent in the aryl moiety showed further increases in the spermicidal activity with an order of potentiation p-bromo>p-fluoro>p-methoxy. The p-bromo substitution of the aryl moiety also unexpectedly showed a significant gain in anti-HIV function. The p-methoxy substituted aryl phosphate derivative WHI-05 (5-bromo-6-methoxy-5,6-dihydro-3'-azidothymidine-5'-(p-methoxyphenyl) methoxyalaninyl phosphate) had an $EC_{50}$ value of 29 μM in sperm motility assays and an $IC_{50}$ value of 0.05 μM in HIV replication assays. The compound WHI-07 with a p-bromo substitution (5-bromo-6-methoxy-5,6-dihydro-3'-azidothymidine-5'-(p-bromophenyl)-methoxyalaninyl phosphate) had an $EC_{50}$ value of 6 μM in sperm motility assays (FIG. 1B, FIG. 2A), which is consistent with a one-log higher potency than that of the detergent spermicide N-9 ($EC_{50}$=81 μM). WHI-07 displayed a potent anti-HIV activity with an $IC_{50}$ value of 0.005 μM in HIV replication assays, which was virtually identical to that of AZT ($IC_{50}$ =0.006 μM) and 439-fold more potent than that of N-9 ($IC_{50}$=2.195 μM) (FIG. 2B).

The removal of the azido group of the pentose ring (WHI-11 and WHI-12) was associated with a reduction in the anti-HIV activity but an improvement of the spermicidal activity for these AZT derivatives (FIG. 1B).

Example 2

Methods

To test the effect of duration of incubation on sperm immobilizing activity (SIA) in the presence of AZT derivatives of the present invention (WHI compounds 01, 03, 05, and 07—see FIGS. 1A and B), motile fractions of sperm ($10^7$/ml) were incubated at 37° C. in 0.5 ml of BWW-0.3% BSA in the presence of 200 μM WHI-01, or 100 μM each of WHI-03, WHI-05, and WHI-07 or 1% DMSO alone. At timed intervals, duplicate aliquots (4-μl) were transferred to two 20 μm Microcell chambers and sperm motility was assessed by CASA. For WHI-01, CASA were performed every 20 minutes for 180 minutes, for WHI-05, every 10 minutes for 70 minutes, and for WHI-03 and WHI-07 CASA was performed every 5 minutes for 40 minutes.

Results

The kinetics of sperm immobilization were fast with the present AZT derivatives. See FIG. 1B. The corresponding times required for 50% motility loss of progressively motile sperm exposed to WHI-05 and WHI-07 (at 100 μM concentration) were 17 minutes (95% CI: 12–26 minutes) and 6 minutes (95% CI: 4–11 minutes), respectively. Complete sperm immobilization was achieved after 60 minutes exposure to WHI-05 and 30 minutes of exposure to WHI-07. By comparison, the sperm motility in control samples remained stable (96±2.5% compared to baseline) during the 180 minutes monitoring period.

Example 3

Methods

The possible effects of seminal plasma on SIA of WHI compounds were studied either in the presence of 10% cell-free seminal plasma in the assay medium or by direct addition (200 µM) of WHI-03, WHI-05, and WHI-07 to dilutions (1:2–1:6) of liquefied donor semen (n=3) in phosphate-buffered saline (PBS) and incubation at 37° C. Following 3 hours of incubation, duplicate aliquots (4-µl) were used for CASA.

To assess the persistence of SIA after removal of WHI compounds, pooled motile sperm ($5\times10^6$) were added to 0.5 ml of assay medium in the presence (100 µM) or absence of WHI-01, WHI-05, and WHI-07 in 1% DMSO. After incubation for 30 and 60 minutes at 37° C., duplicate aliquots were used for sperm motility assessment using CASA. The remaining sperm suspension was washed by the addition of fresh assay medium and centrifugation (500×g for 5 minutes). This supernatant was discarded, and the pellet was resuspended in fresh medium (without WHI compounds) to the original volume and reincubated. Following 30 minutes at 37° C., duplicate aliquots were reassessed for sperm motion parameters by CASA. The results were expressed as the mean of two assessments and were compared to the sperm motion parameters of similarly processed sperm suspensions of motile sperm suspended in medium containing DMSO-only controls.

Results

Direct addition of compounds WHI-05 and WHI-07 to semen diluted in phosphate-buffered saline resulted in complete loss of motility assessed by CASA. Thus, the spermicidal activity was unaffected by the presence of seminal plasma. In order to determine whether the SIA of WHI-05 or WHI-07 was reversible, sperm exposed to 100 µM of either compound for 30 minutes were washed and resuspended in fresh sperm motility assay medium and sperm motility was reassessed by CASA. No recovery in sperm motility was observed, indicating that the drug-induced sperm immobilization was irreversible. The dose- and time-dependent sperm motility loss induced by WHI-05 and WHI-07 was associated with significant changes in the movement characteristics of the surviving sperm, including markedly decreased track speed, path velocity, and straight line velocity.

Example 4

Methods

Because the great majority of spermicidal compounds are believed to immobilize sperm as a result of a detergent-type action on the sperm plasma membrane, the effects of WHI-05 and WHI-07 on sperm plasma membrane permeability were tested by flow cytometric analysis of propidium iodide (PI)-stained sperm and acrosome integrity by examination of FITC-lectin, TOTO-3 iodide, and Nile red-stained sperm using confocal laser scanning microscopy.

The percentages of sperm with an intact acrosome were evaluated by fluorescence microscopy (Olympus BX-60) following fixation and ethanol permeabilization of the sperm pellets and subsequent staining with fluorescein (FITC)-conjugated *Pisum sativum* lectin (Sigma). In positive control sperm, the acrosome reaction was induced by incubating (3 hours at 37° C.) the sperm suspension with 10 µM calcium ionophore (CaI) A23187 (Sigma). Motile sperm ($5\times10^6$/ml) were incubated for 4 hours at 37° C. in the presence and absence of 100 µM each of WHI-01, WHI-03, WHI-05, WHI-07 or N-9 followed by the addition of PI (10 µg/ml) and analyzed by flow cytometry. The percentage of sperm positive for PI were determined by flow cytometry using a FACS Vantage flow cytometer (Becton Dickinson and Co., Mountain View, Calif.). The sperm in the swim-up fractions were identified by their characteristic forward and 90° angle light scattering properties [O. J. D'Cruz and G. G. Haas, Jr. *Fertil. Steril.* 58, 633 (1992)]. All analyses were done using the 488-nm excitation from an krypton/argon laser with a 635-nm band pass filter for PI emission. The percentage of sperm positive for PI staining were determined using cutoff signals for membrane-intact motile sperm.

Ethanol permeabilized and air-dried sperm smears were stained sequentially with the three fluorescent markers, FITC-*Pisum sativum*, TOTO-3 iodide, and Nile red, each marking a different target (acrosome, nucleus, and plasma membrane of permeabilized sperm respectively). Samples were examined under a BioRad MRC-1024 Laser Scanning Confocal Microscope (BioRad Laboratories, Hercules, Calif.) equipped with a krypton/argon mixed gas laser (excitation lines 488, 568, and 647 nm) and mounted on a Nikon Eclipse E800 series upright microscope. The fluorescence emission of fluorescein, TOTO-3 iodide, and Nile red from the acrosomal region, nucleus, and the plasma membrane of sperm after ethanol permeabilization were simultaneously detected using the 598/40 nm, 522 DF32, and 680 DF32 emission/filter respectively. Confocal images were obtained using a Nikon 60× (NA 1.35) objective lens and Kalman collection filter. Digitized images were processed with the Adobe Photoshop software (Adobe Systems, Mountain View, Calif.). Final images were printed using a Fujix Pictography 3000 (Fuji Photo Film Co., Tokyo, Japan) color printer.

High-resolution low-voltage scanning electron microscopy was utilized for topographical imaging of different membrane domains over the sperm head as described [M. H. Stoffel et al. *Molecular. Reprod. Develop.* 34, 175 (1993); S. L. Erlandsen et al. *Scanning* 11, 169 (1989)]. Aliquots ($20\times10^6$) of motile sperm were incubated with DMSO alone (1%), or 100 µM each of WHI-05, WHI-07 or 10 µM CaI in DMSO for 3 hours at 37° C. Washed sperm suspensions were placed on 0.1% poly-L-lysine-coated glass chips and allowed to adhere to the glass over a 60 minute incubation period on ice. The supernatants were decanted, and adherent cells were fixed in 1% paraformaldehyde and 1% glutaraldehyde in 0.14 M sodium cacodylate buffer for 3 hours. To preserve plasma membrane integrity, sperm were post-fixed in 1% osmium tetroxide ($OsO_4$) containing 0.1% ruthenium red in 0.14 M cacodylate buffer for 1 hour at 4° C. All samples were dehydrated through an ascending ethanol series, critical point dried, and coated with approximately 2 nm of platinum using ion beam sputtering with argon (4 mA at 10 ke V; Ion Tech Ltd., Middlesex, England). All samples were examined in a Hitachi S-900 SEM at an accelerating voltage of 2 keV. Sperm were observed under low magnification (×2,000–5000) and representative sperm were photographed under intermediate magnification (×18,000–25,000). In each specimen evaluated, at least 200 sperm were scanned for the intactness of sperm acrosomal region.

For transmission electron microscopy, treated sperm were fixed in 3% glutaraldehyde in 5% sucrose in 0.2 M cacodylate buffer for 3 hours at room temperature. The samples were post-fixed in 1% $OsO_4$, 5% sucrose and 0.1% ruthenium red for 2 hours at 4° C. The samples were dehydrated in ascending ethanol series, and embedded in Spurr's epoxy. Thin sections (90 nm) were prepared on a Reichert-Jung Ultracut E and stained with uranyl acetate and lead citrate. The grids were examined using JEOL-1200 EX II electron microscope (JEOL, Paris) at a accelerating voltage of 60 kV. Sperm were observed under low (×25,000) and high (×100,000) magnification, and representative sperm were photographed. In each specimen evaluated, 100–200 sperm were evaluated for the intactness of sperm head membranes.

Results

Despite complete immobilization of sperm in the presence of WHI-05 and WHI-07, less than 3% of sperm were permeable to PI following 4 hours of incubation with these compounds. In acrosome integrity studies, WHI-05 and WHI-07-treated sperm (similar to sham-treated sperm) remained acrosome-intact (97.0±2.0 and 93.0±5.6 respectively) after 3 hours of incubation at a concentration of 100 $\mu$M, despite a complete loss of motility. Examination of FITC-lectin, TOTO-3, and Nile red-stained sperm by confocal microscopy revealed an intense acrosomal staining with FITC-lectin (green), nuclear staining with TOTO-3 (blue), and membrane staining (red) with Nile red, respectively (FIGS. 3A–3D). In non-acrosome-reacted sperm, the acrosomal regions of the sperm head exhibited a uniform, bright green fluorescence in sperm exposed to vehicle (i.e., 1% DMSO) alone (FIG. 3A), 100 $\mu$M WHI-05 (FIG. 3B), and 100 $\mu$M WHI-07 (FIG. 3C) for 3 hours. By comparison, sperm exposed to 100 $\mu$M of N-9 for 3 hours under identical conditions revealed only acrosome-reacted sperm due to disruption of membrane integrity (FIG. 3D), consistent with previous observations. W. H. Wilborn, D. W. Hahn, J. J. McGuire, *Fertil. Steril.* 39, 717 (1983); A. S. Bourinbaiar, S. Lee-Huang, *Contraception* 49, 131 (1994). Thus, the spermicidal activity of the dual-function AZT analogs was not accompanied by a loss of membrane integrity.

Figure 3:
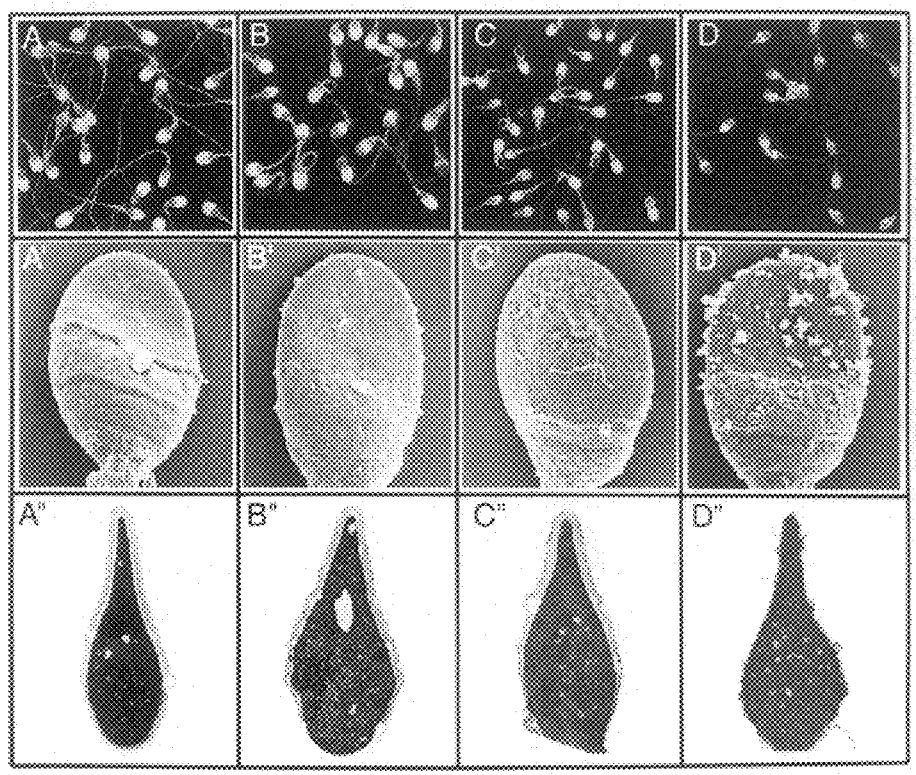
FIG. 3 shows the effects of various AZT derivatives on sperm plasma membrane and acrosomal membrane integrity.

Topographical imaging of drug-treated sperm head by high-resolution low-voltage scanning electron microscopy revealed intact acrosomes (FIGS. 3A'–3D') with smooth contiguous surfaces in sperm exposed to vehicle (FIG. 3A') or 100 $\mu$M WHI-05 (FIG. 3B'), whereas sperm treated with WHI-07 (FIG. 3C') revealed signs of a mild acrosomal membrane ruffling. By comparison, sperm exposed to 10 $\mu$M CaI A23187 revealed characteristic blebbing or vesiculation, fenestration, and loss of plasma and acrosomal membranes (FIG. 3D'). Transmission electron microscopy of the tangential sections of sperm head confirmed the intactness of the plasma membrane, outer, and inner acrosomal membranes of sperm exposed to vehicle (FIG. 3"), WHI-05 (FIG. 3B"), and WHI-07 (FIG. 3C") but not to the CaI A23187 (FIG. 3D") for 3 hours (FIG. 3 bottom panels). Taken together, these results demonstrate that the spermicidal effects of WHI-05 or WHI-07 were not caused by a detergent-type action resulting in disruption of the sperm plasma membrane within the acrosomal region of the sperm head. These features of bromo-methoxy-substituted aryl phosphate derivatives of AZT differ from those of N-9, the most widely used prototype detergent spermicide.

Example 5

Methods

The human sperm-zona recognition and binding assay appears to predict the in vitro and in vivo fertilization outcome. Therefore, the inhibitory effects of WHI-05 and WHI-07 on sperm-egg interaction were next assessed by laser scanning confocal microscopy using intact human zona and two-colored sperm separately labeled with cell permeant DNA-specific dyes, SYBR 14 (green) and SYTO 17 (blue) in a homologous sperm-zona binding assay. Due to the variable number of sperm binding to human eggs, the sperm-zona binding ratio was used to assess sperm-zona binding capacity.

Specifically, human eggs that failed to fertilize in vitro were separately inseminated with a mixture of equal numbers of SYBR 14 (green)- and SYTO 17 (blue)-labeled control sperm or test sperm containing equal numbers of SYBR 14- and SYTO 17-labeled sperm, the latter pretreated with three concentrations (25, 50, and 100 $\mu$M) of the tested compounds. Following coincubation, the number of tightly bound green (SYBR 14) and blue (SYTO 17) sperm were assessed by laser scanning confocal microscopy. Frozen human eggs (n=46) were thawed and rinsed three times in BWW-0.3% BSA, and in BWW-3.5% BSA, before addition of sperm suspension. The process of egg recovery, freezing, thawing, and manipulation in vitro invariably resulted in cumulus-free, non viable eggs. To investigate the effect of WHI-05 and WHI-07 on the binding of human sperm to human zona, motile fractions of capacitated sperm were divided into two aliquots of $10^7$/ml and labeled with two cell permeant DNA-specific dyes (SYBR 14 and SYTO 17). The first aliquot was incubated with 2.5 $\mu$M SYBR 14 (Molecular Probes) and the second aliquot was incubated with 5 $\mu$M SYTO 17. Following 30 minutes of incubation, sperm motility was assessed by CASA. Motile sperm with intensely stained green or blue nuclei were washed twice in BWW and one million motile sperm labeled with SYBR 14 (green) and SYTO 17 (blue) were added to dish containing human zona (n=2) under mineral oil and coincubated for 4 hours. Following extensive washing of eggs to dislodge any loosely adherent sperm, the eggs were mounted on glass slides and examined under a BioRad MRC-1024 Laser Scanning Confocal Microscope as described above. Using fluorescence imaging, the fluorescence emission of SYBR-14 and SYTO-17 localized on the sperm head was simultaneously recorded using 598/40 nm, and 680 DF32 emission/filter respectively. Confocal images of Z-sections were obtained using a Nikon 20× (NA 1.4) objective and Kalman collection filter. Digitized images were processed with the Adobe Photoshop software and final images were printed using a Fujix Pictography 3000 color printer. The number of tightly bound green and blue-colored sperm nuclei adherent to each human egg were counted from the Z-sections of fluorescence images of each egg on all focal planes and expressed as a binding ratio.

Results

Figure 4A:
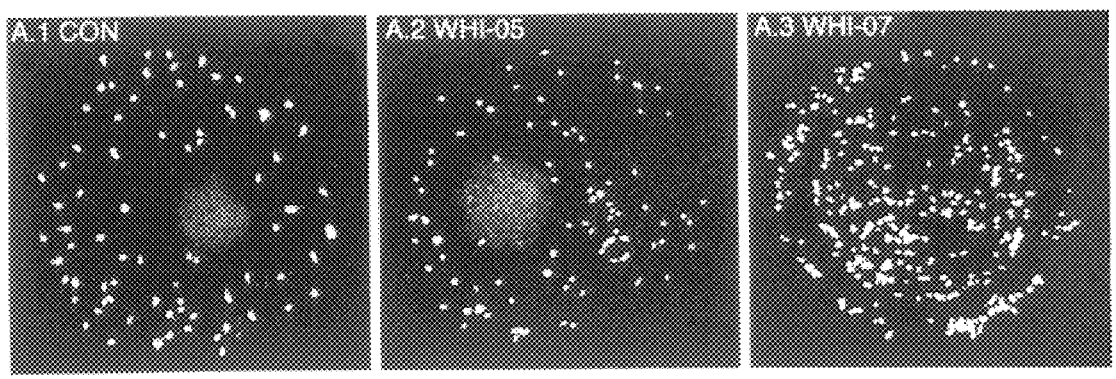
FIG. 4A shows scanning laser confocal microscopy images of sperm-zona binding for control sperm (FIG. A.1), sperm treated with WHI-05 (FIG. A.2), and sperm treated with WHI-07 (FIG. A.3).

The ratio of the number of green and blue sperm bound to human eggs in control and test showed marked differences. The mean sperm-zona binding ratio for control eggs coincubated with SYBR 14 and SYTO 17-labeled control sperm was 1.07. In contrast, mean sperm-zona binding ratios for eggs coincubated with control (SYBR 14) and 25, 50, and 100 $\mu$M WHI-07-treated sperm (SYTO 17) were 0.088, 0.039, and 0.009, respectively. The corresponding mean ratios for sperm treated with 25, 50 and 100 $\mu$M of WHI-05 were 0. 18, 0.07, and 0.10 respectively. FIG. 4A shows the representative sperm-egg binding patterns of green and blue sperm to control egg (A.1) and the test eggs in which the blue sperm were pretreated with either 100 $\mu$M of WHI-05 (A.2) or 25 $\mu$M of WHI-07 (A.3) prior to coincubation with green-labeled sperm. Despite the variable number of sperm binding to individual zona, a clear reduction in the number of blue colored sperm bound to test eggs is apparent when compared with control egg.

Example 6

Methods

The heterologous zona-free hamster egg penetration assay appears to correlate with the in vivo fertilizing capacity of human sperm as well as the ability of human sperm to fertilize intact human eggs in vitro. Therefore, the inhibitory effects of WHI-05 and WHI-07 on sperm-egg interaction were further confirmed by zona-free hamster egg penetration assay.

The fertilizing capacity of human sperm exposed to WHI-05, and WHI-07 was evaluated using zona-free hamster egg penetration assay [Yanagimachi et al. *Biol. Reprod.* 15, 471 (1976)]. Motile fractions of sperm (n=4) obtained by 90–45% Percoll gradient centrifugation and wash were resuspended in BWW-3.5% BSA medium (pH 7.4) and divided into aliquots of $20 \times 10^6$ sperm/ml and allowed to capacitate for 24 hours. Subsequently, sperm were treated at 37° C. for 3 hours with 25 µM or 100 µM concentrations of WHI-05 and WHI-07 (in 0.5% DMSO) under capacitating conditions. After exposure to drugs, the control and WHI-treated sperm suspensions were washed in BWW-3.5% BSA medium. Sperm motility following capacitation and washing in BWW-3.5% BSA medium was assessed by CASA.

Frozen hamster eggs (Charles River Laboratories, Wilmington, Mass.) were thawed and taansferred to 35 mm glass bottom microwells (Mat Tek Corporation, Ashland, Mass.) in BWW medium. To remove zona, the washed eggs were treated with 0.05% trypsin (Irvine Scientific) in BWW medium for 20 min and then transferred to BWW-3.5% BSA medium and washed three times. Fifteen to 45 zona-free eggs per test were transferred in 100 µl of BWW-3.5% BSA medium under mineral oil. Control and test sperm suspensions ($2 \times 10^6$) in <100 µl of BWW-3.5% BSA medium were added and the gametes were coincubated for 4 hours at 37° C. in 5% $CO_2$ in air. Following incubation, the eggs were washed three times with BWW medium to remove the loosely associated sperm. The eggs were fixed and stained, as previously described [EI-Danasouri et al. *Fertil. Steril.* 59, 470 (1993)]. Bound and decondensed fluorescent sperm were viewed with a Olympus BX 60 epifluorescent microscope equipped with an excitation filter BP 360-370 and DM 400 barrier filter BA 420. The number of sperm bound per egg, the number of swollen sperm heads per egg, and the percentage of penetrated eggs were determined for control and test sperm. An egg was considered penetrated when it contained at least one swollen sperm head in the cytoplasm.

Results

Preincubation of capacitated sperm with either compound resulted in significant inhibition ($P<0.001$) of sperm binding to zona-free eggs (FIG. 4B). Similarly, the penetration rate of human sperm to zona-free hamster eggs following exposure to increasing doses of WHI-05 or WHI-07 showed marked inhibition (41% to 100% inhibition when compared with control). Thus, pretreatment of human sperm with spermicidal aryl phosphate derivatives of AZT resulted in a dose-dependent loss of the ability to bind and penetrate zona-free hamster eggs as well as inhibition of binding to human eggs.

Example 7

Methods

Because fertilization in vivo is dependent on successful sperm transport through the female genital tract, we next determined whether exposure of sperm to the WHI-07 in vivo affected the subsequent fertility outcome. Hormonally primed adult female Swiss (CD-1) mice were artificially inseminated with motile epididymal sperm via the cervix with and without prior intravaginal application of WHI-07 in a cream base. Females were examined 8 days later for the presence or absence of embryos in uteri.

More particularly, adult (5–6 months old) female CD-1 mice were superovulated by an intraperitoneal injection (i.p.) of 5 IU of pregnant mare's serum gonadotropin followed by an i.p. injection of 5 IU of human chorionic gonadotropin 46–48 hours later. Mice were randomly assigned to one of the two treatment groups (27 or 24/group); vehicle controls [cream base (Taro Pharmaceuticals, Hawthorne, N.J.) with 1% DMSO], or test group (cream base with 1% WHI-07 in 1% DMSO) and given intravaginally (50 µl) prior to artificial insemination. Caudae epididymal sperm were obtained from proven breeder adult CD-1 male (5–6 months old) [B. Hogan, R. Beddington, F. Costantini, E. Lacy, Eds., *Manipulating the Mouse Embryo* (Cold Spring Harbor Laboratory Press, Plainview, N.Y., 1994] and suspended in a modified Krebs Ringer-bicarbonate medium (M2; Gibco-BRL) supplemented with pyruvate, lactate, and glucose. Sperm were capacitated in M2 medium-5% BSA for 1 hour prior to use. For each experiment cauda epididymal sperm pooled from 25 male mice and adjusted to $1-2 \times 10^6$ motile sperm/5 µl were used for insemination. A 50 µl volume/mouse was ejected through a 1 ml syringe with a blunted 18 gauge needle. Preparations were analyzed for sperm concentration, motility, and sperm motion parameters by CASA using software designed for oval sperm head morphology (Hamilton Thorne). On day 8, individual females representing the control and test group were killed and their uteri were examined for the presence or absence of embryos. A total of three independent fertility experiments were performed.

Results

The results of three fertility trials are summarized in Table 1. In mice given WHI-07 intravaginally prior to artificial insemination, the percentage of fertility rate was drastically reduced when compared to controls (7.6% vs 38.4%; $P<0.001$) indicative of the inability of WHI-07-exposed sperm to reach the site of fertilization.

TABLE 1

Fertility of female mice after artificial insemination of sperm via cervix with and without intravaginal application of WHI-07.

| Experiment | No. of mice inseminated/ group* | No. of control mice fertile† (%) | No. of WHI-07-treated mice fertile (%) |
|---|---|---|---|
| 1 | 27 | 10 (37.0) | 2 (7.4) |
| 2 | 27 | 11 (40.7) | 1 (3.7) |
| 3 | 24 | 9 (37.5) | 3 (12.5) |
| Total | 78 | 30 (38.4) | 6 (7.6)‡ |

*Animals were sacrificed on day 8 of the expected pregnancy.
†Fertility was determined by examining the uteri for the presence or absence of embryos.
‡Significantly different from control group ($p < 0.001$).

Example 8

Methods

Any proposed improvement in vaginal contraceptives should take into account the non-specific membrane toxicity caused by the detergent-type action of the currently available vaginal contraceptives. This can damage the vaginal tissues, rendering the subject more susceptible to infection by sexually-transmitted diseases such as HIV. Therefore, the local tissue alterations and inflammatory response to repetitive intravaginal application of N-9 versus WHI-07 in mice was compared. Two groups of 15 adult female Swiss (CD-1) mice were treated for 5 (group A) or 20 (group B) consecutive days with either 5% N-9, 5% WHI-07, or control vehicle in a cream base, and the cervicovaginal tissue sections were examined for histopathological changes and influx of inflammatory cells (FIG. 5). The cervicovaginal region consisted of a stratified squamous epithelium overlying a vascular submucosa. The thickness of the epithelium varied depending on the four stages of the estrous cycle.

In particular, 30 female CD-1 mice, 6 months old were randomly divided into two groups (A and B). Each group was further divided into three subgroups of 5 mice. Mice from group A were treated for 5 days and mice from group B for 20 days via daily intravaginal application of a cream base (Taro Pharmaceuticals) supplemented with 1% DMSO alone (control), 5% WHI-07 in 1% DMSO or 5% N-9. After 5 and 20 days respectively, mice were killed by cervical dislocation, and tissues from the genitourinary tract were fixed in 10% buffered formalin. To determine the degree of inflammation and membrane integrity of squamous epithelia, conventional paraffin-embedded sections (6-µm) were prepared and stained with hematoxylin and eosin and observed under 300× magnification with a Leica microscope interfaced with an image analysis system (Scion), and images were transferred to Adobe Photoshop software for printout. The four stages of the estrous cycle were determined histologically.

Indirect immunofluorescence assay and confocal microscopy were used to identify the neutrophil infiltrates in the squamous epithelia of cervicovaginal sections of control, WHI-07, and N-9-treated mice. Cervicovaginal tissue sections were deparaffinized, hydrated through graded ethanol, and immunostained with a rat mAb (Cederlane Laboratories Ltd., Westbury, N.Y.) directed against mouse neutrophils (clone 5120-26.1-110). Following antigen retrieval by heating (93° C. for 10 min in 10 mM sodium citrate buffer, pH 6.0), sections were preincubated with 10% normal goat serum in PBS, treated with optimal dilution (5 µg/ml) of the mAb followed by FITC-conjugated goat anti-rat IgG (Pierce Chemical Co., Rockford, Ill.). Each incubation step lasted 60 min with 5 min PBS washes between each step. The slides were counterstained with PI (1µg/ml), washed in deionized water, mounted in anti-fade (BioRad), and visualized by laser confocal microscopy as described above. Negative controls were carried out by replacing the primary mAb with PBS or using rat IgG2 as control mAb.

Results

Figure 5A:
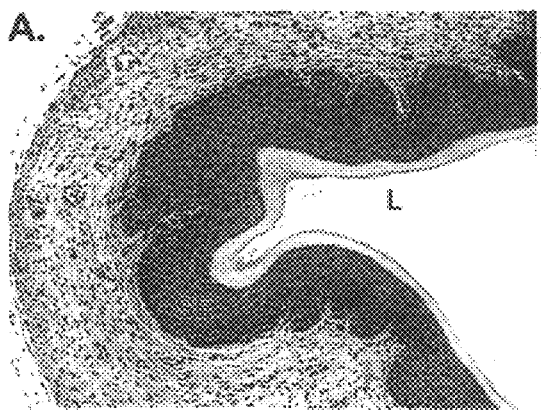
FIGS. 5A–D illustrate the reduction in inflammation of cervicovaginal tissues from treatment with an AZT derivative of the present invention versus N-9.
Figure 5B:
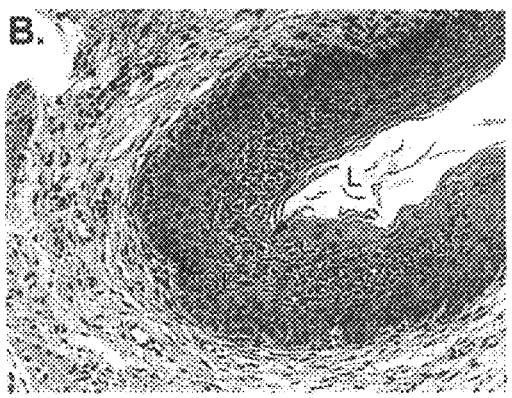
Figure 5C:
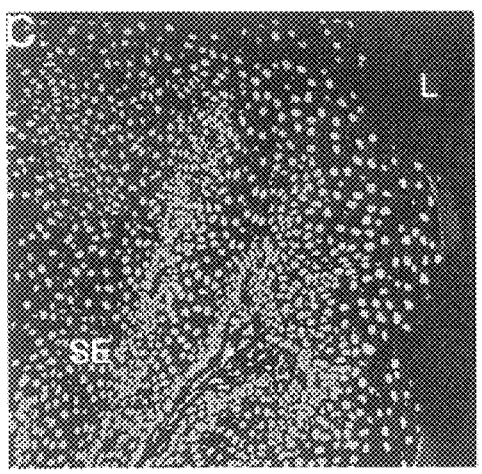
Figure 5D:
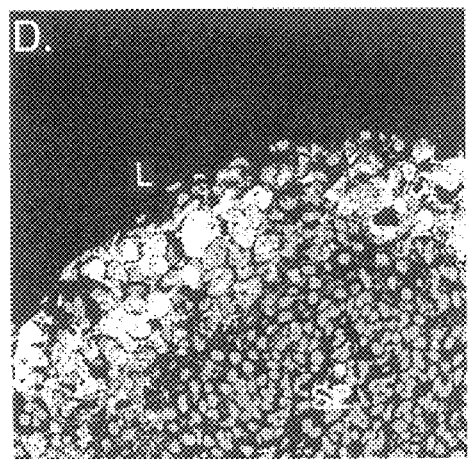

Similar to the 10 vehicle alone-treated control mice, none of the 10 mice treated with WHI-07 for 5 days or 20 days exhibited any significant inflammatory response or membrane disruption of the squamous epithelia (FIGS. 5A and E). By contrast, disruption of the epithelial lining and an inflammatory response with influx of neutrophils in the 10 squamous epithelia of cervicovaginal crypts were evident in 9 of 10 mice given N-9 intravaginally (FIGS. 5B and E), consistent with previously published observations in rats. See Tryphonas and Buttar, Toxicol. Lett., 20, 289 (1984). Two color laser scanning confocal fluorescence images of the cervicovaginal epithelia of WHI-07 and N-9-treated sections with a monoclonal antibody specific to mouse neutrophils revealed absence of neutrophils in the stratified squamous epithelial crypts of WE-07-treated specimens (FIG. 5C) and intense positive staining (green color) in the squamous epithelia of N-9-treated tissue section (FIG. 5D). These studies demonstrate that, unlike N-9 treatment, intravaginal application of WHI-07 in a cream base does not cause any membrane disruption or an acute inflammatory response in the cervicovaginal epithelial crypts.

The substituted pyrimidine derivatives of the present invention unexpectedly exhibit potent spermicidal and anti-HIV activity profiles. As a result, they may be usefull as contraceptives capable of preventing the sexual transmission of HIV, especially as vaginal contraceptives. As such, the AZT derivatives of the present invention will be particularly useful for providing fertility control for women who are at high risk for acquiring HIV by heterosexual transmission.

While a detailed description of the present invention has been provided above, the invention is not limited thereto. The invention described herein may be modified to include alternative embodiments, as will be apparent to those skilled in the art. All such alternatives should be considered within the spirit and scope of the invention, as claimed below.

We claim:

1. A compound of the formula:

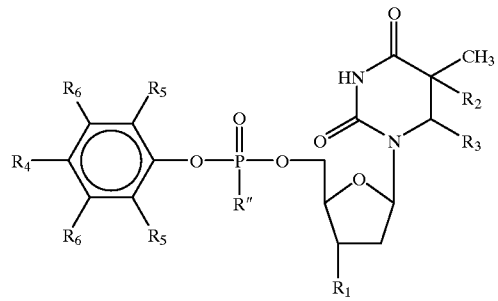

where: $R_1$ is $N_3$;
$R_2$ is Br;
$R_3$ is OMe;
$R_4$ is selected from Br, H, F, OMe, and $NO_2$;
$R_5$ and $R_6$ are hydrogen; and
R" is an N-amino acid residue;
or a pharmaceutically acceptable salt or ester thereof.

2. The compound of claim 1, wherein $R_4$ is Br.
3. The compound of claim 1, wherein $R_4$ is H.
4. The compound of claim 1, wherein $R_4$ is F.
5. The compound of claim 1, wherein $R_4$ is OMe.
6. The compound of claim 1, wherein $R_4$ is $NO_2$.
7. A compound of the formula:

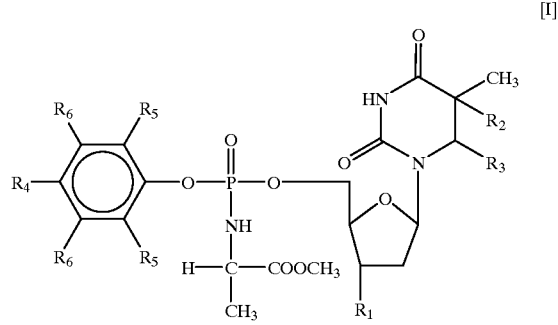

[I]

where: $R_1$ is $N_3$;
$R_2$ is Br;
$R_3$ is OMe;
$R_4$ is selected from Br, H, F, OMe, and $NO_2$; and
$R_5$ and $R_6$ are hydrogen;
or a pharmaceutically acceptable salt thereof.

8. The compound of claim 7, wherein $R_4$ is Br.
9. The compound of claim 7, wherein $R_4$ is H.
10. The compound of claim 7, wherein $R_4$ is F.
11. The compound of claim 7, wherein $R_4$ is OMe.
12. The compound of claim 7, wherein $R_4$ is $NO_2$.
13. A method of inhibiting conception in a mammal, comprising contacting mammalian sperm with an effective spermicidal amount of a compound of the formula:

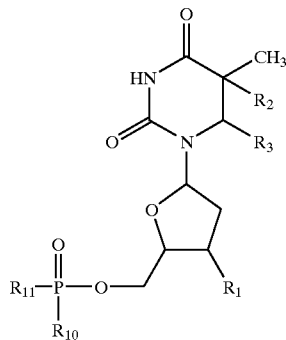

where $R_1$ is H, $N_3$, halogen, CN, COOH, $NH_2$, NH—$CH_3$, NH—$OCH_3$, NH—Ph, NH—COPh or NH—$CH_2$—Ph, $R_2$ is halogen, $R_3$ is $C_{1-3}$ alkoxy, and $R_{10}$ and $R_{11}$ are the same or different and are selected from an N-amino acid residue, OH, SH, $NH_2$, $OR_{12}$, and $SR_{12}$, wherein $R_{12}$ is a substituted or unsubstituted $C_{1-4}$ alkyl or a substituted or unsubstituted aryl;

or a pharmaceutically acceptable salt or ester thereof.

14. The method according to claim 13, wherein $R_2$ is bromo and $R_3$ is methoxy.

15. The method according to claim 13, wherein $R_1$ is $N_3$.

16. The method according to claim 13, wherein $R_{11}$ is a group of formula:

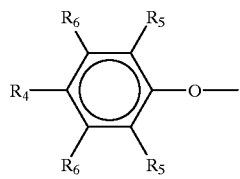

where $R_4$, $R_5$, and $R_6$ are the same or different and are selected from the group consisting of hydrogen, methyl, ethyl, fluoro, chloro, bromo, iodo, trifluoromethyl, nitro, cyano, methoxy, trifluoromethoxy and ethoxy.

17. The method according to claim 16, wherein $R_4$ and $R_5$ are the same or different and are selected from the group consisting of hydrogen, fluoro, bromo and methoxy.

18. The method according to claim 16, wherein $R_5$ and $R_6$ are hydrogen, and $R_4$ is selected from hydrogen, fluoro, bromo, and methoxy.

19. The method according to claim 13, wherein $R_{10}$ is an N-amino acid residue.

20. A pharmaceutical composition, comprising:

an effective spermicidal amount of a compound of the formula:

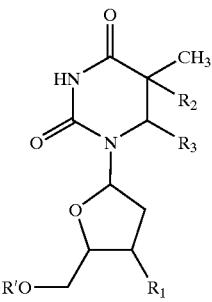

wherein $R_1$ is $N_3$, $R_2$ is halogen, $R_3$ is $C_{1-3}$ alkoxy, and

R' is selected from the group consisting of a fatty acid acyl group, and a group of the formula:

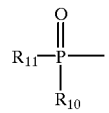

wherein $R_{10}$ and $R_{11}$ are the same or different and are selected from an N-amino acid residue, OH, SH, $NH_2$, $OR_{12}$, and $SR_{12}$, wherein $R_{12}$ is a substituted or unsubstituted $C_{1-4}$ alkyl or a substituted or unsubstituted aryl;

or a pharmaceutically acceptable salt or ester thereof; and a carrier, diluent or vehicle suitable for contraceptive use.

21. The composition according to claim 20, wherein $R_2$ is bromo and $R_3$ is methoxy.

22. The composition according to claim 21, wherein the R' is a group of the formula:

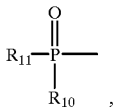

wherein $R_{11}$ is a group of formula:

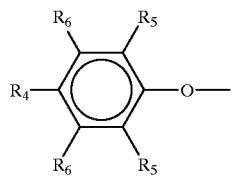

wherein $R_4$, $R_5$, and $R_6$ are the same or different and are selected from the group consisting of hydrogen, methyl, ethyl, fluoro, chloro, bromo, iodo, trifluoromethyl, nitro, cyano, methoxy, trifluoromethoxy and ethoxy.

23. The composition according to claim 22, wherein $R_4$ and $R_5$ are the same or different and are selected from the group consisting of hydrogen, fluoro, bromo and methoxy.

24. The composition according to claim 22, wherein $R_5$ and $R_6$ are hydrogen, and $R_4$ is selected from hydrogen, fluoro, bromo, and methoxy.

25. The composition according to claim 22, wherein $R_{11}$ is an N-amino acid residue.

* * * * *

UNITED STATES PATENT AND TRADEMARK OFFICE
CERTIFICATE OF CORRECTION

PATENT NO. : 6,407,078 B1 Page 1 of 1
DATED : June 18, 2002
INVENTOR(S) : D'cruz et al.

It is certified that error appears in the above-identified patent and that said Letters Patent is hereby corrected as shown below:

Title page,
Item [56], References Cited, OTHER PUBLICATIONS, in the Balzarini, J. et al. reference, the title should be replaced to read -- "Differential Patterns of Intracellular Metabolism of 2', 3'-Didehydro-2', 3'-dideoxythymidine and 3'-Azido-2', 3'-dideoxythymidine, Two Potent Anti-human Immunodeficiency Virus Compounds" --

Please insert the following reference: -- Hao, Z. et al., "Factors Determining the Activity of 2', 3'-Dideoxynucleosides in Suppressing Human Immunodeficiency Virus In Vitro", *Molecular Pharmacology*, 34 (4): 431-435 (October 1988). --

Column 2,
Line 30, "mobility" should read -- motility --

Column 25,
Line 57, "WE-07" should read -- WHI-07 --

Signed and Sealed this

Seventeenth Day of December, 2002

JAMES E. ROGAN
*Director of the United States Patent and Trademark Office*